US010180388B2

(12) United States Patent
Wagner

(10) Patent No.: US 10,180,388 B2
(45) Date of Patent: Jan. 15, 2019

(54) SCANNING INFRARED MEASUREMENT SYSTEM

(71) Applicant: 1087 SYSTEMS, INC., Cambridge, MA (US)

(72) Inventor: Matthias Wagner, Cambridge, MA (US)

(73) Assignee: 1087 SYSTEMS, INC., Cambridge, MA (US)

( * ) Notice: Subject to any disclaimer, the term of this patent is extended or adjusted under 35 U.S.C. 154(b) by 0 days.

(21) Appl. No.: 15/048,705

(22) Filed: Feb. 19, 2016

(65) Prior Publication Data

US 2017/0016813 A1 Jan. 19, 2017

Related U.S. Application Data

(60) Provisional application No. 62/118,005, filed on Feb. 19, 2015.

(51) Int. Cl.
*G01N 15/14* (2006.01)
*G02B 21/00* (2006.01)
(Continued)

(52) U.S. Cl.
CPC ......... *G01N 15/1436* (2013.01); *G01N 15/00* (2013.01); *G01N 15/06* (2013.01); *G01N 15/147* (2013.01); *G01N 15/1434* (2013.01); *G01N 15/1475* (2013.01); *G01N 21/35* (2013.01); *G01N 21/3577* (2013.01);
(Continued)

(58) Field of Classification Search
CPC .................................................. G01N 15/1436
See application file for complete search history.

(56) References Cited

U.S. PATENT DOCUMENTS 4,885,473 A 12/1989 Shofner et al.
9,377,400 B2 * 6/2016 Wagner .................. G01N 21/39
(Continued)

FOREIGN PATENT DOCUMENTS

GB 502971 A 5/1939
GB 2507959 5/2014
GB 2507959 A 5/2014

OTHER PUBLICATIONS

International Search Report for PCT/IB2016/000295, dated Oct. 14, 2016, 19 pages.
(Continued)

*Primary Examiner* — David P Porta
*Assistant Examiner* — Jeremy S Valentiner
(74) *Attorney, Agent, or Firm* — McAndrews, Held & Malloy, Ltd.

(57) ABSTRACT

An analyzer of a component in a sample fluid includes an optical source and an optical detector defining a beam path of a beam, wherein the optical source emits the beam and the optical detector measures the beam after partial absorption by the sample fluid, a fluid flow cell disposed on the beam path defining an interrogation region in the a fluid flow cell in which the optical beam interacts with the sample fluid and a reference fluid; and wherein the sample fluid and the reference fluid are in laminar flow, and a scanning system that scans the beam relative to the laminar flow within the fluid flow cell, wherein the scanning system scans the beam relative to both the sample fluid and the reference fluid.

34 Claims, 9 Drawing Sheets

(51) Int. Cl.
*G01N 21/3577* (2014.01)
*G01N 21/39* (2006.01)
*G01N 21/53* (2006.01)
*G01N 15/06* (2006.01)
*G01N 21/35* (2014.01)
*G01N 15/00* (2006.01)
*G01N 21/3581* (2014.01)
*G01N 21/552* (2014.01)
*G01N 15/10* (2006.01)

(52) U.S. Cl.
CPC ............ *G01N 21/39* (2013.01); *G01N 21/53* (2013.01); *G02B 21/006* (2013.01); *G02B 21/008* (2013.01); *G02B 21/0032* (2013.01); *G02B 21/0036* (2013.01); *G02B 21/0064* (2013.01); *G01N 21/3581* (2013.01); *G01N 21/552* (2013.01); *G01N 2015/0065* (2013.01); *G01N 2015/0687* (2013.01); *G01N 2015/0693* (2013.01); *G01N 2015/1006* (2013.01); *G01N 2015/1443* (2013.01); *G01N 2015/1447* (2013.01); *G01N 2015/1488* (2013.01); *G01N 2015/1497* (2013.01); *G01N 2021/399* (2013.01); *G01N 2201/068* (2013.01); *G01N 2201/105* (2013.01)

(56) References Cited

U.S. PATENT DOCUMENTS

| | | | | |
|---|---|---|---|---|
| 2004/0079893 | A1* | 4/2004 | Dietz | G01N 15/1475 250/458.1 |
| 2012/0122084 | A1* | 5/2012 | Wagner | C12N 5/0612 435/6.1 |
| 2012/0225475 | A1* | 9/2012 | Wagner | G01N 15/14 435/288.7 |
| 2015/0276588 | A1* | 10/2015 | Marshall | G01N 21/1717 250/343 |
| 2016/0004060 | A1* | 1/2016 | Simpson | G02B 21/0084 348/80 |

OTHER PUBLICATIONS

Transmittal of IPR for Application No. PCT/IB2016/000295, dated Aug. 22, 2017.

* cited by examiner

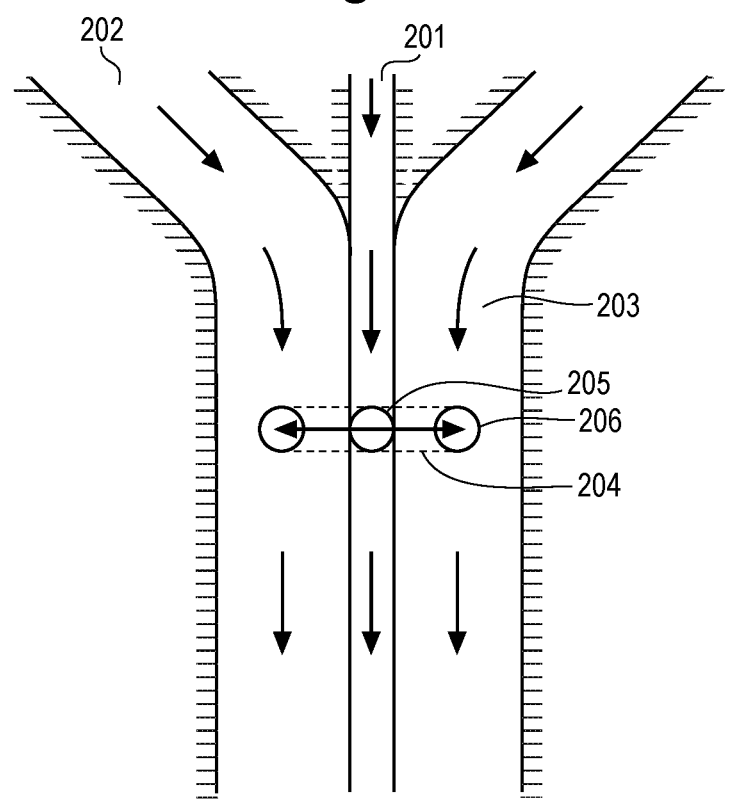

(SIDE VIEW)　　　　　　(FRONT VIEW)

Fig. 11
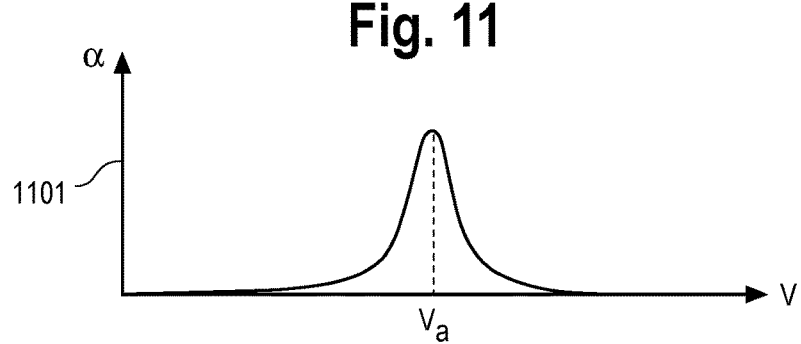
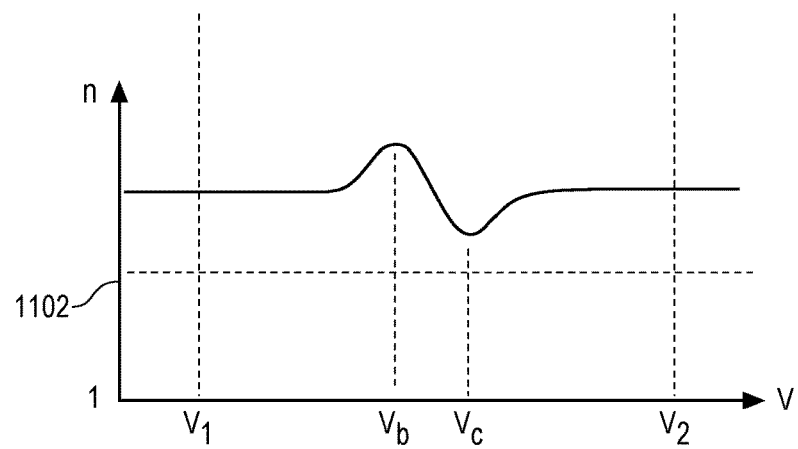
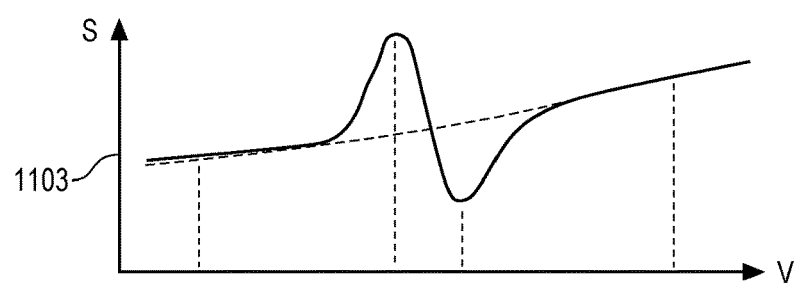
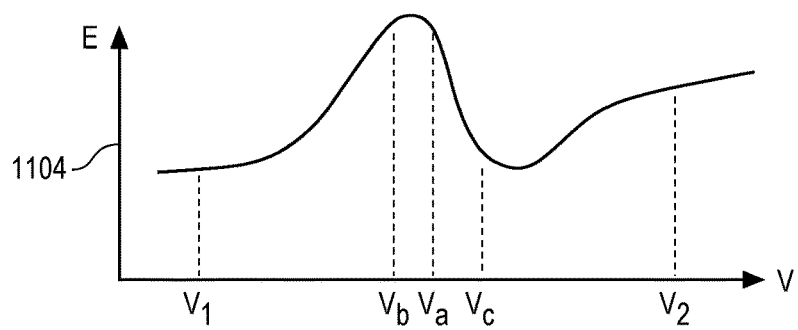

SCANNING INFRARED MEASUREMENT SYSTEM

CROSS REFERENCE

This application claims benefit under Title 35, United States Code, Section 119(e) of U.S. provisional patent application Ser. No. 62/118,005 filed Feb. 19, 2015. The 62/118,005 is hereby incorporated by reference into this application. U.S. application Ser. No. 13/894,831 entitled "Cytometry System with Interferometric Measurement" is also incorporated by reference in its entirety into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to infrared spectroscopy and more specifically a system by which infrared lasers, including QCLs, may be used to measure liquid samples, and provides significant advantages in terms of signal-to-noise ratio in measuring chemical composition of these liquids; as well as resulting in a system that is very stable in the face of laser or other optical train changes.

2. Any discussion of the prior art throughout the specification should in no way be considered an admission that such prior art is widely known or forms part of common general knowledge in the field.

BACKGROUND

Infrared spectroscopy is a valuable, well-known tool for chemical characterization of gaseous, liquid and solid substances because compounds have distinct absorption "fingerprints" in the mid-infrared region, with absorption bands corresponding to vibrational energies of molecular bonds.

In theory, infrared spectroscopy should be a very valuable tool for analyzing liquid samples for applications including, but not limited to: medical liquid analysis (blood, urine, saliva, etc.) for diagnostics or substance detection; industrial or food/beverage process control; pollutant detection; etc.

A major barrier to broader application of infrared spectroscopy to liquid samples has been the high inherent absorption of many liquids in the infrared. For example, water has strong infrared absorption, making analysis of aqueous solutions difficult. A number of tools have been developed to circumvent this issue, for example: the use of attenuated total reflection (ATR) prisms and other surface-grazing optical techniques; drying of samples before analysis; and the use of liquid-liquid extraction processes to transfer solutes from one liquid to another, more infrared-transparent liquid. Each of these introduces potential complexities and inaccuracies into measurements of liquids.

New and improved light sources in the infrared, including quantum cascade lasers (QCLs) offer significantly higher power at specific wavelengths of interest than traditional "glo-bar" (incandescent broadband thermal emitting) sources. This higher power potentially enables absorption measurements in thicker liquid samples, while maintaining sufficient power throughput to allow reasonable signal-to-noise for measurement of chemical concentrations in the sample. Measurements can then be performed with one or more wavelengths, with one or more "signal" wavelengths at absorption peaks of interest, and possibly wavelengths designed to provide reference or baseline levels (off-peak). Multiple wavelengths may be achieved using multiple lasers, or through the use of wavelength-tunable sources.

For detection of low concentrations of compounds in liquids, or subtle changes in chemical makeup, the incremental infrared absorption corresponding to concentrations of interest may be extremely small. Therefore even with higher power transmission, there remains the problem of detecting small absorption signals against a high background.

A solution employed to measure low concentrations in spectroscopy is the use of reference wavelengths. For example, sample transmission at the wavelength corresponding to an absorption peak of a substance of interest is measured, together with the transmission at two nearby wavelengths, one higher and one lower. A "baseline" is then computed using the reference wavelength transmissions, and the transmission at the "peak" wavelength is divided by this baseline. This type of baseline adjustment can compensate for factors such as sample thickness, broad absorption by other compounds, and detector responsivity changes. In the case of broadband infrared sources, it also compensates—over a limited wavelength range—for changes in source output. For example, such referencing will drastically reduce effects from changes in temperature of a conventional black-body thermal source. Indeed, this allows traditional Fourier-Transform Infrared (FTIR) instruments equipped with glo-bar sources—or even using broadband radiation from synchrotron sources—to produce spectral data that may be locally baselined (in wavelength) to accurately determine chemical content.

Such baselining techniques, however, may be significantly less effective with infrared laser sources such as those that could deliver higher power to penetrate thicker liquid samples. Laser sources are inherently narrowband, resonant devices, rather than broadband emitters. Their output—power, wavelength, bandwidth, polarization and spatial beam properties—can be highly sensitive to device and operating conditions including current, temperature, aging, and feedback (from reflections). Moreover, any changes in these conditions may cause highly discontinuous changes in output. Moreover, these changes will not be consistent from one laser to another, or even from one wavelength to another in the case of a broadband or tunable laser.

As a result, changes between illumination at the "peak" (absorption, of a target compound) wavelength and "reference" wavelengths may be very large compared to the incremental absorption from compounds of interest.

One method used for gaseous spectroscopy is the use of tunable lasers that scan through an absorption peak in a short time. This is the core concept behind tunable diode laser absorption spectroscopy (TDLAS) that is already used in commercial instruments. In gaseous samples, absorption peaks are typically very narrow ($<<1$ cm$^{-1}$) and high. This means a very narrow tuning range may be used (often $<1$ cm$^{-1}$ in wavenumber terms) to cover reference and peak wavelengths. This tuning may be performed quickly, and with minimum variation in laser conditions.

In liquid systems, on the other hand, absorption bands become far broader, with lower peak absorptions. This requires tunable systems to cover a far broader range ($>10$ cm-1, for example)—this is difficult to do consistently. For example, mode transitions within the laser may occur inconsistently, leading to sharp changes in power and other beam characteristics at the wavelengths of interest.

Similarly, multiple discrete sources operating at wavelengths over the required range may individually vary in their emission characteristics over time and operating conditions, leading to apparent changes in "reference" and "peak" transmission and errors in reported chemical concentrations.

Furthermore, although it is possible to integrate reference power detectors that monitor laser power prior to the sample, such reference schemes require beam splitting optics which will introduce new optical artifacts such as fringing into the system; moreover, the power split off by these optics may be different from the power delivered to the sample as a result. In addition, such a reference channel will not account for optical effects within the sample and sample chamber—which can be particularly strong in a coherent, laser-based system.

BRIEF SUMMARY OF THE INVENTION

The present invention describes a system by which infrared lasers, including QCLs, may be used to measure liquid samples, and provides significant advantages in terms of signal-to-noise ratio in measuring chemical composition of these liquids; as well as resulting in a system that is very stable in the face of laser or other optical train changes.

The system includes a liquid handling system that combines reference and sample liquids into a laminar flow that travels through a microfluidic channel (or "cuvette") that is infrared-transparent. The system further comprises optics to deliver light from one or more infrared lasers into this channel; infrared light is partially absorbed by the liquids in the channel according to its chemical constituents, path length, temperature and optical characteristics. The system further comprises a scanning subsystem which scans the beam relative to the laminar flow within the channel, such that the beam scans over both reference and sample fluids. The system further comprises one or more detectors that measure the light that has been partially absorbed by the liquid in the channel, while the scanning subsystem scans the light over both sample and reference liquids.

Importantly, a microfluidic channel with laminar flow allows liquids to be presented in nearly identical configurations to the light source, in close proximity to one another, such that measurements of sample and reference fluids can be made within a short period of time during which the system remains stable. In addition, the close proximity of the fluids to one another in a common flow ensures they are presented in nearly identical conditions (pressure, temperature, flow rate, etc.).

Detection

In some embodiments, AC-coupled detectors may be used to measure the differential absorption between reference and sample liquids at one or more wavelengths as the scanning subsystem scans the beam between the liquid streams. The scan rate may be adjusted to optimize detector and system signal-to-noise ratio (SNR), for example placing it above most 1/f noise, but still within the high-response range for the detector and its amplifying circuitry. Various well-known schemes for extracting and filtering and signal at a specific frequency may be used to optimize SNR. Inherently change-sensitive ("AC") detectors such as pyroelectric detectors may be used; as may other thermal detectors such as thermopiles, or photovoltaic detectors such as cooled or uncooled InGaAs or HgCdTe detectors. Pyroelectric detectors may provide an advantage of very high saturation flux (power per unit area) while remaining sensitive to small changes in infrared light as a result of differential absorption between reference and sample fluids.

Scanning

Scanning may be achieved by scanning one or more beams optically over the sample, or translating the sample relative to the beam(s). Many subsystems for scanning beams over samples have been produced for microscopy, and similar subsystems may be utilized in the present invention.

Lasers

One or more infrared lasers may be used in the present invention to generate one or more wavelengths of interest. In some cases, a single fixed-wavelength laser could be used to interrogate a specific absorption peak of a compound that is not present in the reference liquid, but potentially present in the sample liquid. As the beam scans between reference and sample fluids, the magnitude of the change detected on the detector allows calculation of the concentration of the compound in the sample.

In other cases it may be helpful—because of interfering, non-target compounds, or because better concentration accuracy is desired—to use multiple wavelengths, including at least one "signal" wavelength (measuring an absorption peak of interest) and one or more "reference" wavelengths. In such a configuration, these wavelengths may be delivered simultaneously from multiple lasers (which may be in a single-chip array, or in discrete devices), or from one or more lasers that are wavelength-tunable.

When multiple wavelengths are used simultaneously, these may be separated after transmission through the sample by means of thin film filters, diffraction gratings, or similar devices. Alternatively they may be modulated in such a manner as to make their signals separable in the detection system.

Relatively broadband laser sources, such as Fabry-Perot lasers, may be used, and component wavelengths split from one another after optically before detection.

The present invention may utilize wavelengths and lasers throughout the infrared range, including but not limited to the near-infrared and mid-infrared regions where many compounds have characteristic absorption peaks, but also in the THz range where stronger laser sources such as QCLs are being developed.

Reference Liquids

The reference liquids used in the present invention may be of several forms. In the most basic configuration, the reference liquid consists of a pure sample of the medium contained in the sample liquid—i.e. containing none of the target compound. For example, if the goal is to measure impurities (such as hydrocarbons) in water, the reference liquid may be distilled water, or a known "clean" sample of water from the site being monitored.

In other cases, the reference liquid may contain the compound of interest at a desired level; for example in an industrial process where a compound is added to a liquid medium, a reference liquid mixed to exact concentration in a laboratory may be used. Therefore any signal detected as the beam in the system is scanned between sample and reference indicates a deviation from the desired level. The phase, or sign, of this signal will indicate whether there is too much or too little of the compound, and magnitude will indicate the error level. As with many embodiments of the present invention, multiple compounds may be measured in this manner at multiple wavelengths. For example, an entire "panel" could be run in continuous, real-time fashion in a brewing process—against a "golden sample" of the product.

In another example, a medical liquid such as blood plasma may be analyzed in the present invention against a standard reference that contains target levels of certain constituents, for example glucose. Any deviations may be measured with high contrast.

In other applications, the reference liquid may be a "before" sample, while the sample liquid is "after," where chemical change is monitored over time to measure degradation, for example. For instance, oil condition in machinery or electrical equipment may be monitored in this manner to track degradation and call for oil changes or other preventative maintenance. Again, the samples are presented in a laminar flow that allows nearly identical measurement conditions, and high contrast and SNR resulting from the scanning measurement.

In other embodiments, the present invention may be used in a configuration where a reference fluid is split into two streams, and one stream is exposed to gaseous, liquid, or solid samples that react with it, alter its chemical composition, or introduce external compounds into it. The result of this interaction is now the "sample" liquid, which is then measured as described above. Examples of such interactions include compounds dissolved from the external sample into the sample liquid, including liquid-liquid extractions, gas-to-liquid extraction, solid-to-liquid extraction. For example, such a system may enable measurement of trace amounts of a compound on the surface of a solid, by first dissolving this compound in a known liquid, and then measuring the resulting sample liquid against a pure sample of the liquid medium, with high contrast as described herein.

In other embodiments, the sample liquid or stream may in fact consist of the compounds formed at the interface of two liquids flowing in a laminar system, as a result of reactions between those two liquids. In this case, the interface region ("sample") may be measured at various lengths into the flow chamber, and the reaction rates/concentrations deduced from the rate of growth of the infrared absorption signal from the sample stream.

In other embodiments, the reference liquid may be pre-impregnated with compounds other than those being measured, in order to facilitate accurate measurement of liquid flow parameters. For example, it may be desirable to measure the exact cross-section of the sample liquid vs. reference liquid in the laminar flow channel, in order to determine sample concentrations with maximum accuracy. For this purpose, the reference liquid includes a marker that will be missing from the sample liquid, allowing its omission to be detected in the sample. This marker does not necessarily have to function in the infrared—it could, quite simply, be a color dye that is monitored optically in the visible range (so long as the dye's absorption peaks in the infrared do not interfere with the measurement).

In certain applications, much of the reference liquid may be separated and re-used at the end of the laminar flow section. Sufficient reference liquid in the proximity to the sample liquid (enough to account for diffusion) is stripped and discarded with the sample liquid, and the remainder of the reference liquid is recirculated.

Flow

In many embodiments, a single laminar stream of sample liquid surrounded by reference liquid (either in 2 or 3 dimensions) is required. Such a laminar flow, and the methods and fluidic devices for producing it, are well known from the fields of microfluidics and cytometry.

In other embodiments, it may be advantageous to produce a multiplicity of laminar sample and reference streams, alternating across the flow channel. Such a configuration may allow higher SNR in the signal resulting from scanning.

For high transmission in the infrared, it may be desirable to use relatively thin flow channels, for example <1 mm, or in many cases <100 microns (um), <50 um, <25 um or even <10 um—depending on the transmission of the fluid, and the fluid dynamic parameters required to maintain a laminar flow.

The scanning beam and surface angles of the fluidic chamber may be arranged so as to minimize surface reflections which may interfere with measurements by variable constructive or destructive interference and even potentially feedback to the laser. As most infrared laser sources are inherently polarized, the surfaces oriented such that P polarized light experiences no reflection as it passes through the measurement chamber.

The present invention may utilize either transmissive or transflective (where light passes through the liquid, reflects, re-passes through the liquid and then back to a detector) configuration.

The present invention may incorporate surface-grazing/evanescent coupling absorption spectroscopy techniques such as the use of photonic crystals that are in contact with the sample and reference fluid flows, or more commonly, ATR prisms where the measurement face forms one side of the fluid flow channel. In such architecture, scanning is still achieved by moving the beam (which enters the ATR, and reflects at least once off the surface in contact with the fluid) perpendicularly relative to the laminar fluid flow over the measurement face of the ATR crystal.

Wavelengths

The present invention may be used throughout the infrared and Terahertz range where laser sources are available. Specifically, it may be used in the near-infrared (0.75-1.4 um), short-wave infrared (1.4-3 um), mid-wavelength infrared (3-8 um), long-wavelength infrared (8-15 um), and far-infrared (20-1000 um) regimes where compounds have characteristic vibrational absorption lines, and laser as well as detector components have been developed capable of being used as described above.

QCLs

Quantum cascade lasers (QCLs) may offer specific advantages for use in the present invention. They may be fabricated to emit at wavelengths throughout the mid-infrared as well at the Terahertz ranges where the present invention may be used to measure liquid properties. They are available in multiple formats, including discrete narrowband single-wavelength devices, broadband (Fabry-Perot) emitters which may optionally be combined with wavelength-selective or dispersive elements to select one or more specific wavelength bands, wavelength-tunable subsystems, and QCL arrays which may emit a number of wavelengths from a single-chip device. All of these forms of QCL may be used in the context of the present invention.

Applications

Applications of the present invention include, but are not limited to:
  measurement of medical fluids including blood plasma, urine, or saliva against standard reference fluids for diagnostic purposes, or to monitor for controlled substances; this may include the measurement of blood glucose level;
  measurement of water samples against reference water samples to test for/determine concentrations of pollutants;
  measurement of biological samples against reference media to measure levels of DNA, RNA, proteins, sugars, lipids, cellular nutrients and metabolites; this includes measurement of liquids which have surrounded cells or tissue (such as cancer cells, stem cells, embryos) to measure uptake of nutrients and/or production of metabolites; measurement of DNA levels in polymerase chain reaction (PCR) tests;

measurement of liquid samples from food, drink, or pharmacological production processes against standard reference liquids to provide feedback for production parameters, measure completion, or measure contamination;

measurement of liquids used in electrical or mechanical machinery against standard reference liquids to measure wear and schedule preventative maintenance or replacement;

measurement of airborne chemicals through trapping in a liquid stream, and comparison to a pure reference liquid;

measurement of chemical composition in solids through exposure to a liquid, and comparison of that liquid to a pure reference liquid;

measurement of liquids such as milk against a standard reference to determine nutritional and fat content, and other parameters; measurement of potable liquids such as olive oil against a known reference to determine authenticity and purity; measurement of potable liquids against reference liquids to measure potentially harmful impurities.

Generalized Liquid Scanning System

More generally, the present invention may be extended to allow measurement of liquid-based samples either in flow or non-flow environments. The essential elements remain the same: and infrared laser source such as a QCL (which may operate at one or more wavelengths), a mechanism for scanning the beam produced by this source over a liquid-based sample, which may include concentration gradients (the target of this measurement system) which result in a variation in the extinction of infrared light as it interacts with the sample (where the aforementioned scanning converts this spatial variation into a temporal variation in a specific frequency range), a mechanism to guide the resulting infrared light (after scan-modulated interaction with the sample) to a detector subsystem which includes an AC-sensitive detector designed to measure changes in infrared light intensity corresponding to the scanning frequency range; the output of this detector subsystem being used to calculate concentrations of target substances in the liquid. This scanning may be performed in 1- or 2-dimensions on a liquid-based sample as described below.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

FIG. 2 shows presenting the liquid sample in a flow configuration that allows referencing against a standard.

FIG. 10b shows an example of the present invention used to measure dispersed contents within the liquid sample of FIG. 10a;

FIG. 11 shows further explanation of the scattering measurement that may be employed in certain embodiments of the present invention where particles, cells, droplets or other inclusions are dispersed in the liquid sample;

DETAILED DESCRIPTION

Figure 1A:
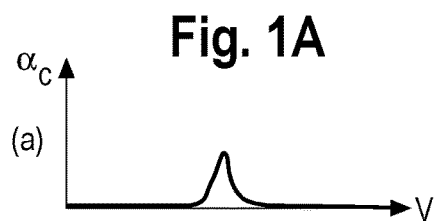
FIG. 1a shows the absorption of the target compound.
Figure 1B:
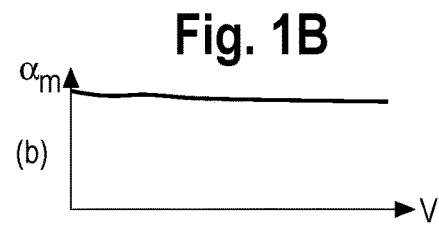
FIG. 1b shows the absorption of the medium in which the compound is dissolved.
Figure 1C:
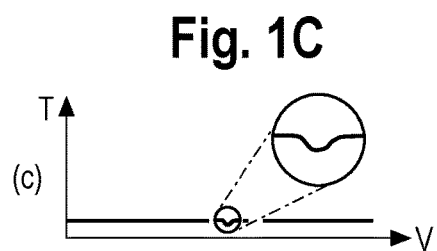
FIG. 1c shows the transmission through the liquid sample.
Figure 1D:
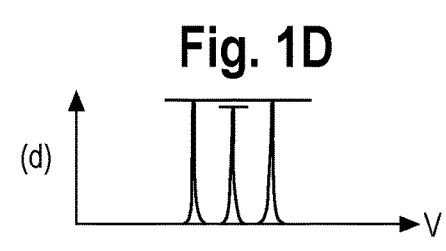
FIG. 1d shows an idealized case where three narrowband infrared laser sources are used to measure reference and signal absorption frequencies, compute peak absorption, and thereby concentration of the compound.
Figure 1E:
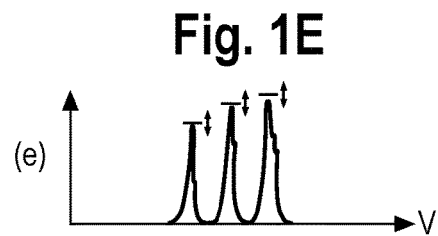
FIG. 1e shows the reality version of such systems.
Figure 3A:
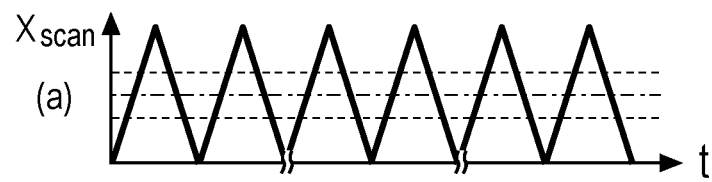
FIG. 3a shows an example of a scanning pattern.
Figure 3B:
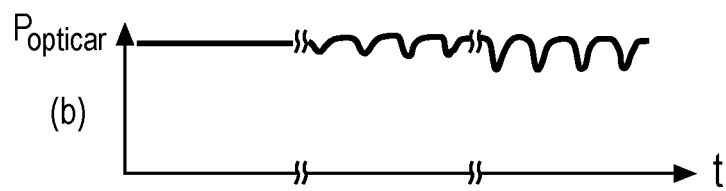
FIG. 3b schematically shows the transmitted optical power as the beam is scanned over the channel, at three different concentration levels.
Figure 3C:
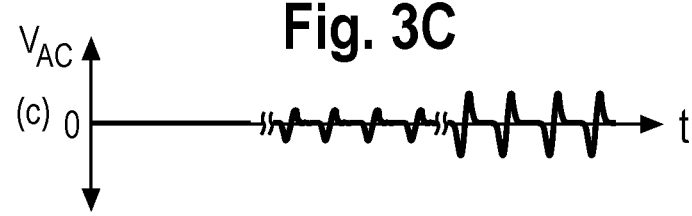
FIG. 3c shows the output of an example detector circuit in response to these optical transmission changes.
Figure 3D:
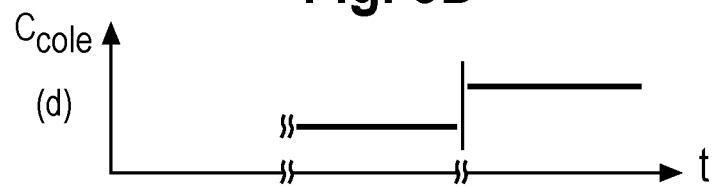
FIG. 3d shows the concentration of the target compound calculated in the current system.

FIG. 1 illustrates an example of spectroscopy of a compound in a liquid. FIG. 1a shows the absorption of the target compound, in its pure form, as a function of frequency. In this simplified example, a single absorption peak is shown. FIG. 1b shows the absorption of the medium in which the compound is dissolved; in this case, a uniform high absorption is shown (which is the case, for example, for water over certain infrared ranges). Note the liquid medium may in fact have a very complex absorption profile with multiple absorption peaks, and may in fact consist of many intermingled chemical components. The present invention is, in fact, very well suited to handle such scenarios where the medium has complex absorption patterns, as it inherently removes common components between a reference and sample fluid, and therefore the features of the medium in which the target compound is carried (taking the example where the target is in solution). FIG. 1c then shows the transmission through the liquid sample, including both the medium and target compound. Note the overall transmission may be very low (as is the case with aqueous solutions in the mid-infrared), and the incremental absorption due to the compound of interest may be extremely small. Moreover, with a broadband infrared source such as a glo-bar or even synchrotron, the power density per frequency is very low, so the total power delivered to the frequency range where the compound absorbs is very low. This makes accurate measurement of samples in liquid very challenging using conventional sources. FIG. 1d shows an idealized case where three narrowband infrared laser sources are used to measure reference and signal absorption frequencies, compute peak absorption, and thereby concentration of the compound. FIG. 1e shows the reality of such systems—the laser power may vary significantly over frequency, as may their bandwidths/band shapes, spatial modes, etc. These characteristics may also vary significantly with time, temperature, vibration/shock, and other environmental parameters. This means the variation in laser characteristics overwhelms differential absorption from the compound of interest in many cases, even when great lengths are taken to stabilize or calibrate the system.

The present invention overcomes this issue by presenting the liquid sample in a flow configuration that allows referencing against a standard, as shown in FIG. 2. A laminar flow is established which combines the sample fluid with a reference fluid, and these flow side by side through the optical measurement zone. In the measurement zone, an infrared beam is translated (scanned) back and forth over the reference and sample liquids. A laminar flow system, which may be a microfluidic system in many applications, ensures that there is not strong mixing between the sample and reference liquids; the parameters for such a flow (dimensions, flow rate) are well established in the art. The measurement zone should typically be set in a region where there is a stable slow, but where significant diffusion of the compound(s) of interest between the sample and reference has not occurred (in some cases this may be desirable, as noted above). The scanning range should be large enough to optically sample the sample and reference liquids completely, but typically limited in range in order to maintain substantially identical optical path conditions in the system. In some cases the channel itself may be translated across the beam, while in others the beam will be scanned over the channel. In some cases, a fluidic chamber may be pre-charged with a laminar flow, the flow terminated, and then the chamber measured optically before significant diffusion occurs. The chamber itself may be part of a disposable unit, built using low-cost microfluidic manufacturing techniques. This unit may include the reference liquid on-board, as well as in some cases any liquid required to prepare the sample fluid. Note that while the flow cell shown in FIG. 2 has two reference flows on either side of a sample flow (which is often helpful for "centering" the flow), other configurations are possible. A minimal configuration would merge one sample liquid flow with a single reference liquid flow (2 inputs), and scanning would occur at the interface of these. More complex flows could include multiple reference and sample flows interleaved.

A brief additional description of the example fluidic measurement unit shown in FIG. 2 is as follows: a sample fluid 201 runs into the chamber together with one or more reference fluids 202 (one branch is marked) into a chamber with laminar flow 203. In the optical measurement region 204 a beam is scanned across the reference fluid as well as sample fluid, with at least one region 205 where it substantially measures absorption of the sample fluid, and one region 206 where it substantially measures absorption in the reference fluid.

FIG. 3 schematically represents the operation of the system as it is used to determine concentration of a target compound in the sample fluid, in this case using a single infrared laser source and single detector. FIG. 3a shows an example of a scanning pattern (triangular in this case, though many other known optical scanning patterns may be used, including 2-dimensional scan patterns) where the infrared beam is scanned from reference fluid, through sample fluid, and back to reference fluid. Note that the beam does not necessarily need to pass through the entire sample stream; it could simply oscillate on one edge of the flow between sample and reference fluids. A feedback loop may be used to continuously center the scan optimally on the edge or center of the sample flow—this feedback may use the absorption of the compound of interest, or other unrelated absorption peaks that are always present (including reference compounds added to the reference or sample liquid, as described above). FIG. 3b schematically shows the transmitted optical power as the beam is scanned over the channel, at three different concentration levels. Note the incremental absorption as the beam passes over the sample may be extremely small. Note in some cases, the present invention may in fact be used to measure the absence or reduction of the absorption peak in the sample fluid. FIG. 3c shows the output of an example detector circuit in response to these optical transmission changes. The detector and/or circuit are configured in this case to use an AC detection mode, where only changes in optical power are registered (as the derivative of that power with time). Such a configuration may provide significant advantages where the incremental absorption is very small—it effectively removes the high baseline, and any common absorption features. Note that in some cases where the absorption of the target compound is high, a conventional DC detection scheme may be used. Even when an AC detection scheme is used, it may be useful to measure DC power, either with the same detector (through a split AD/DC circuit) or with a separate detector, so as to normalize the AC signal by the DC optical power (which will take into account laser power and overall liquid and system transmission, among other long-term changes). Inherently AC detectors such as pyroelectric detectors, which are low-cost and are stable over temperature, may be used. In fact, a whole class of well-known detectors and circuits that have been developed for FTIR instruments (which measure AC signals resulting from a scanning interferometer) may be employed in the present invention. FIG. 3d shows the concentration of the target compound calculated in the current system. This concentration could be calculated from a single scan, or from the aggregate of many scans, depending on the accuracy and real-time characteristics required for the application.

Figure 4:
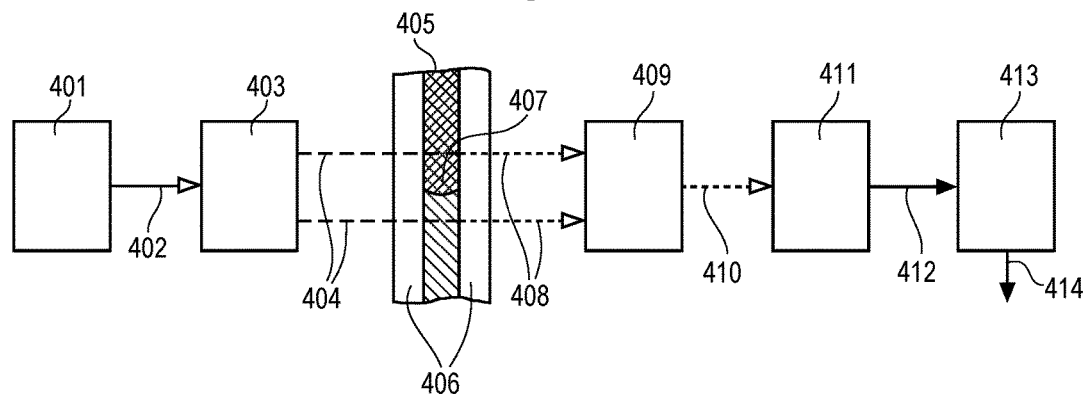
FIG. 4 shows a generalized version of the present invention.

FIG. 4 shows a generalized version of the present invention. A mid-infrared laser source 401 produces mid-infrared light 402 that is scanned relative to the sample chamber 405 by a scanning system 403. This scanning system may in fact be a system that translates the sample chamber in relation to a stationary beam. Here the scanning system is shown to scan the beam over a range of positions 404 that pass through the chamber windows 406 and the contained liquid sample 407. As the beam is scanned through different portions of the liquid sample, which may contain concentration gradients of target analytes, the amount of mid-IR light transmitted at specific wavelengths may vary by transmitted beam position 408. A de-scanning mechanism 409 serves to deliver all of this light substantially to the same detector subsystem 411. The de-scanning mechanism may be one and the same as the scanning mechanism, in the case where the sample chamber is translated to achieve the scanning, or in some cases a lens with appropriate characteristics may be used to focus substantially all the scanned light onto the detector element. The de-scanned light 410 reaching the detector subsystem 411 therefore is modulated by scanning it through the liquid sample 407, with all other conditions held substantially identical through the course of the scan. The detector subsystem 411 is an AC-coupled detector system that either uses a detector such as a pyroelectric detector which is responsive only to changes in optical power, and/or employs a circuit to remove any DC component of the de-scanned light 410 reaching the detector subsystem. Therefore gain can be applied in order to amplify effects from small changes in transmission due to scanned concentration gradients, without saturating the output of the detector subsystem. The output 412 of the detector subsystem is then processed by a computing unit 413 that calculates absorption and potentially concentrations 414 as a function of position in the sample.

The core elements of the invention are: the use of mid-infrared lasers such as QCLs to produce light at wavelengths corresponding to compounds of interest in the liquid-based sample; a method of scanning this light relative to the sample in order to modulate transmission according to local concentrations of these compounds; a method of delivering the transmitted light to an AC-coupled detector system which amplifies these transmission differentials that result from scanning; and a system to compute absorption and potentially relative concentrations within the sample.

Detectors: examples of detectors include mercury-cadmium-telluride (MCT) photoconductive or photovoltaic detectors run in AC-coupled amplification circuits, or pyroelectric detectors—which are inherently AC-coupled in nature. For many applications, pyroelectric detectors may be well suited because of their AC-coupled nature, very high saturation power, temperature insensitivity, and low cost. Importantly, pyroelectric detectors remain linear over a wide range of powers (whereas MCT detectors saturate). In particular in a case where mid-infrared lasers are used, there is often plenty of power, and the present invention allows concentration measurements through the detection of small changes in this power (rather than absolute DC power measurement).

Note that the detector subsystem, in addition to the AC-coupled primary detector(s), may additionally comprise a DC level detector that monitors the overall transmitted mid-IR light, and is used to normalize the AC signal. Such DC-level detection allows adjustment for overall laser power, system transmission, liquid sample thickness, etc.

Sampling: while many embodiments will use a transmission-type design where the scanned beam (where "scanned" is understood to mean either the beam scanning over the sample, or the sample being scanned relative to the beam) is transmitted through the sample chamber and the sample. However, the present invention extends to designs employing "transflection" (where the beam passes through the sample, is reflected, and passes through the sample once more on its path to exit), as well as surface-sampling techniques such as attenuated total reflection (ATR) prism-based designs where the beam reflects off a surface in contact with the liquid sample and evanescently couples into it, evanescent waveguide designs, and designs where resonant surface coatings (such as photonic crystal or metamaterial designs) in contact with the sample amplify interaction between the mid-infrared light and the sample.

Scanning: the beam scanning frequency and pattern will vary by configuration and application. Preferably, the scanning allows the signal corresponding to the absorption, and therefore the concentration gradient, to be shifted to a frequency well above low-frequency noise sources (1/f noise, etc.) and variations (temperature fluctuations in the mechanics or laser, etc) in the system and thereby avoid many of the pitfalls of static (DC) transmission measurements systems. For example, the scanning frequency can be at least approximately 1 Hz, 10 Hz, 100 Hz, 1000 Hz, 10000 Hz or higher as the detector subsystem allows. The scanning frequency should also fall into a range where the detector employed has sufficient response. For example, pyroelectric detectors are thermal detectors, and therefore have a roll-off in signal with frequency that may be pronounced over 100 Hz. The detector circuit should also be designed—and potentially optimized—for the scanning frequency. Well-known "lock-in amplification" techniques may be applied to isolate the signal resulting from the scanning; the phase of the detected signal relative to the scanning may be used to further refine the signal. For example, in cases where a known interface between two fluids (say, side-by-side laminar flows of a sample and reference fluid) is scanned, the change in transmitted intensity at that interface may be isolated from other scanning-related optical artifacts. Alternatively, a baseline may be established by running the scan over a section of sample known to have no concentration gradients. Various other digital filtering techniques that are well known may be applied after the amplified detector signal is captured in an analog-to-digital converter.

Figure 5:
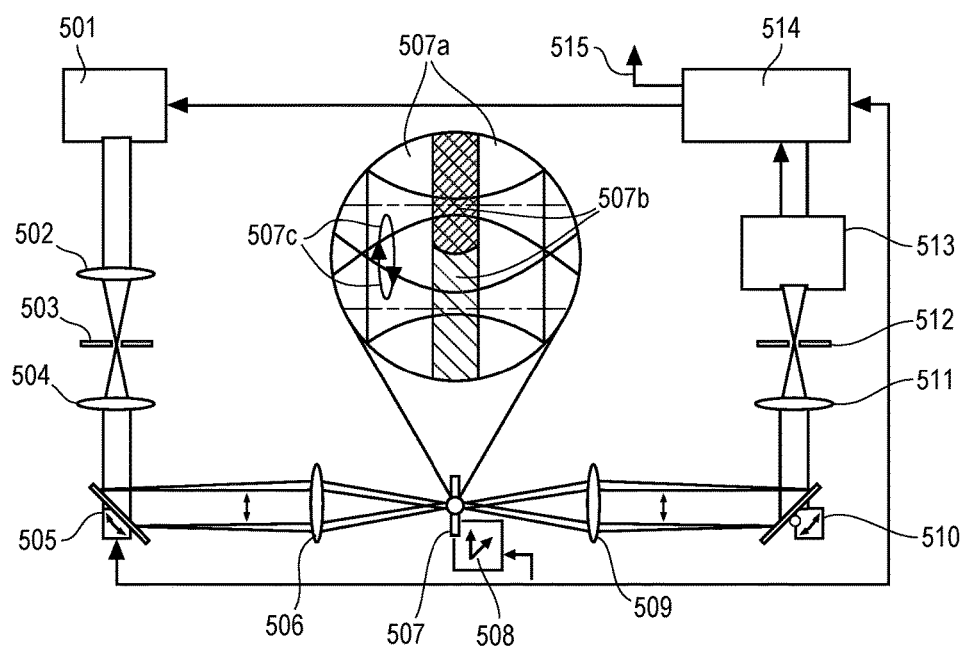
FIG. 5, FIG. 6 and FIG. 7, show other embodiments of the present invention.

FIG. 5 shows another embodiment of the present invention. A mid-infrared laser source 501 (which may produce one or more wavelengths in the mid-infrared) is focused by a lens 502 through a spatial filter 503 which is designed to "clean up" the mid-infrared beam, with the transmitted light well-suited for focusing into a well-defined spot (despite any variation in the output of the laser, such as different modes); the filtered light is re-collimated by lens 504 and then scanned over a range of angles by scanner 505. The scanner may scan in 1 or 2 axes. The scanned light is focused by lens 506 onto sample holder 507. The scanned beam 507c (showing two beam positions within the scan) passes through the sample chamber windows 507a and the contained liquid-based sample 507b (which in this example, shows two regions with differing concentration of a target compound). The sample holder may optionally be mounted on a translation stage 508 with one or more translation axes in order to position the sample relative to the scanning beam. For example, a "Z" translation (substantially parallel to the axis of the beam) may be used to optimally focus the beam on the sample within the sample holder, and thereby get maximum contrast during the scan; "X" and or "Y" translation may be used to position the sample such that the scanning beam traverses specific features having concentration gradients of interest (for example, the boundary between two liquid flows, or the location of a biological cell). A capturing lens 509 re-collimates the transmitted mid-IR light and a de-scanning mirror 510 redirects the mid-IR light such that the light remains incident on the AC-coupled detector system 513 with minimal intensity modulation when there is no concentration gradient in the sample. A lens 511 focuses the light, optionally through a spatial filter 512, onto the AC-coupled detector system 513. The detector signal(s) are relayed to a computing system 514 that computes absorption gradients, and potentially concentrations 515 of analytes, in the sample. This system may also control laser operation (power and wavelength, for example), scanning and de-scanning modules, and translation stage(s).

Liquids: the present invention may be used to measure liquid-based samples of various types, including liquid flows with concentration gradients, biological cells in liquid, biological tissues in un-dried state, dispersions of droplets or solid particles in liquids. Each sample will ideally have concentrations gradients over the scale scanned by the present invention, so as to induce a change in the amount of light transmitted, and therefore an AC signal on the detector. The change in signal may in fact result from the displacement of the medium (for example, water) by a solute or dispersed material, or scattering as a result of the difference of refractive index between a cell, droplet or solid particle and the surrounding medium.

Scattering Measurement: in some embodiments, the present invention may measure or calculate scattering resulting from particles or droplets dispersed in the liquid sample—again by scanning between regions with more and fewer of such particles/droplets, or between regions where such particles/droplets change in nature. In such embodiments, scattering with increase as a function of droplet/particle diameter and refractive index, which is a function of its composition and wavelength. Through the use of appropriate spatial filters before and after the sample, it is possible to isolate or remove scattered light, and thereby calculate scattering from particles/droplets in the liquid in order to deduce average diameter (assuming some chemical composition). With multiple wavelengths around infrared absorption peaks for droplet/particle constituents, it is additionally possible to estimate both chemical composition as well as droplet size as it results from resonant Mie scattering (rapid change in scattering as a result of rapid change in refractive index around a resonant absorption peak for a particular compound).

For example, in measurements of hydrocarbons in water, often many of the hydrocarbons are not dissolved in the water, but form droplets dispersed in the water. The present invention may be used to measure a sample of water with potential hydrocarbon contamination in a laminar flow side-by-side with a pure water reference, by scanning the beam (or equivalently, the sample) back and forth across the interface between these parallel flows. Measurements can be made at several wavelengths, including a peak absorption wavelength for hydrocarbons, but also a non-peak wavelength. Non-peak wavelength signal will indicate scattering and water displacement; the differential between peak and non-peak will indicate total hydrocarbon concentration. Additionally, if wavelengths on either edge of the absorption peak are measured, the differential in scattering loss (as a result of resonant Mie scattering) may be used to calculate dispersed hydrocarbon characteristics. Therefore the present invention may be used to measure both dissolved and dispersed hydrocarbons in a water sample, and distinguish between these.

Figure 6:
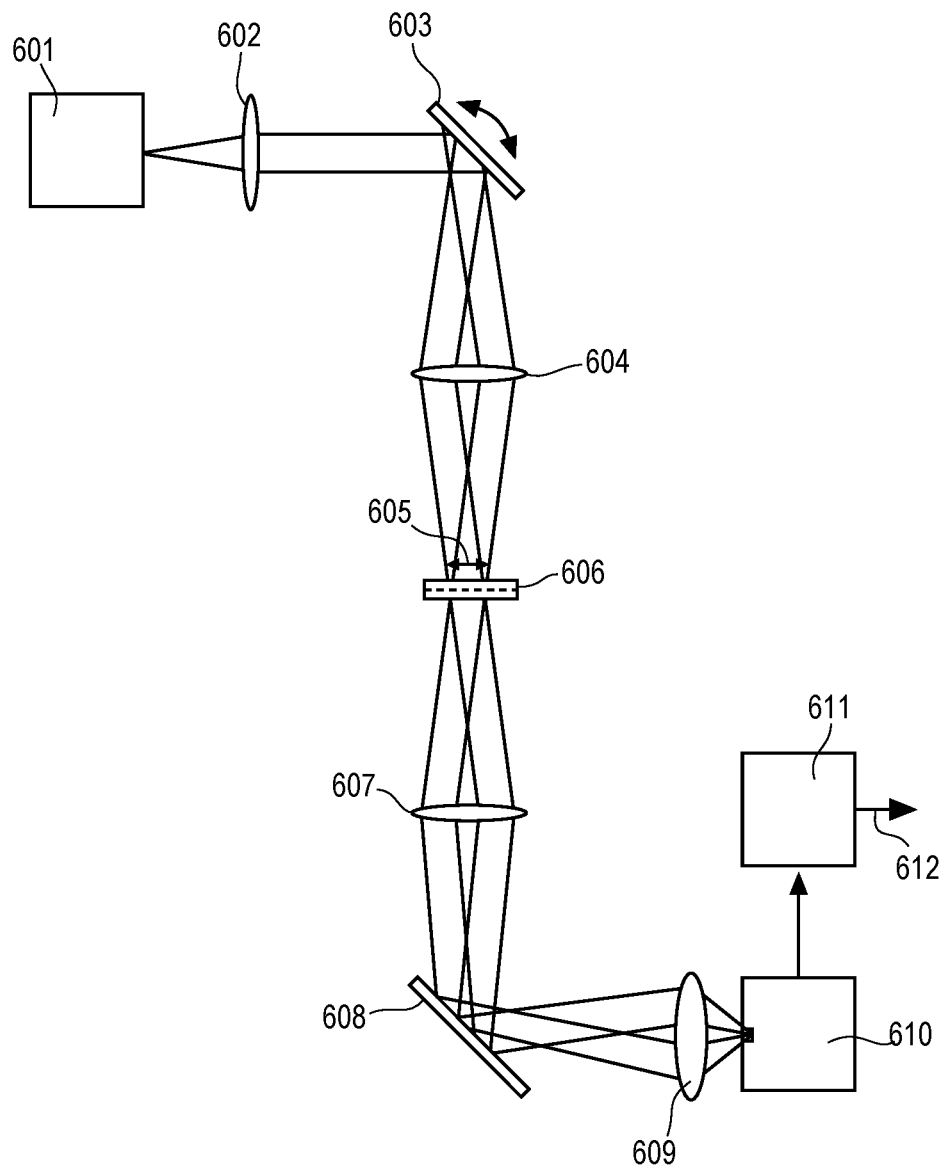

FIG. 6 shows another embodiment of the present invention; this example shows a system where "de-scanning" onto a single detector element is accomplished with the use of a short focal length lens 609. A complete description is as follows: a mid-infrared laser source such as a QCL (which can be a single-wavelength device, emit multiple wavelengths, or have a tunable wavelength) 601 is collimated through lens 602 (all lenses described in this invention may be refractive or reflective-type lenses), and then scanned using scanner 603 over a range of angles, before being focused on the liquid sample chamber 606 by lens 604. The sampling spot therefore is scanned over a section of the liquid sample as indicated by 605; upon transmission through the liquid sample it may be differentially attenuated depending on chemical concentrations within the sample and the interrogating wavelength(s); the beam scanning converts such gradients into a periodic power fluctuation in the transmitted light. A collimating lens 607 re-collimates the light, and in this example a fixed folding mirror 608 redirects the collimated beam to a short focal length lens 609. The function of the short focal length lens is to focus the transmitted infrared light onto the detector 610. Generally a small detector area is desired, as noise grows with the square root of area. In this example, a short focal length is used at the detector compared to the focal length of focusing lenses 604, 607. As a result, the motion of the beam spot on the detector will be a fraction of the motion of the spot on the sample, allowing a reasonable scan distance on the sample while maintaining focus on the surface of a small detector. The signal from the detector subsystem is used by a computer unit 611 that calculates absorption and possibly concentrations, which go to output 612.

Detector: In some cases it may be desirable to use detectors with asymmetric dimensions (for example, an elongated rectangle), and to orient this detector with its long axis along the scan direction, to facilitate complete (or at least consistent) beam capture throughout the scan cycle. In some cases detector arrays may be used in the present invention; however, the scanning should not result in beam spot(s) moving from detector element to detector element (which would cause very large signal swings not related to concentration gradients in the sample).

Beam Arrays: in some embodiments, multiple beam spots may be used and scanned simultaneously across the sample. These may be multiple spots of identical wavelength, split in order to take advantage of increased performance from the use of an array of detectors (where the light from each beam remains focused on its corresponding detector element throughout the modulating scanning described herein). Alternatively, if an infrared laser array such as the distributed feedback (DFB) QCL described by Capasso et al (DFB Quantum Cascade Laser Arrays, Benjamin G. Lee et al., IEEE Journal of Quantum Electronics, vol. 45, no. 5, May 2009) is used, each spot may correspond to a different wavelength of interest, and be relayed to its corresponding detector after interacting with the sample. In one embodiment, QCL DFB array with wavelengths corresponding to one or more absorption peaks for a target compound, plus one or more reference wavelengths to measure background absorption, can be projected onto a liquid chamber containing a laminar flow with adjacent sample liquid and reference liquids. The laser array is oriented such that the spots from the array run parallel to the flow of the liquid, and then the modulating scanning described herein scans these spots perpendicular to the fluid flow, and across any concentration gradient formed by the interface between the sample and reference fluids. After interacting with the fluid and being absorbed according to wavelength and concentration, each of these spots is relayed to a corresponding AC-coupled infrared detector (in many cases part of an array, such as a pyroelectric detector array). The modulation of each detector signal resulting from the modulating scanning corresponds to the differential absorption between reference and sample liquid at a particular wavelength; from these signals the concentration of one or more compounds within the sample liquid may be calculated.

2D Scanning: in the present invention "modulation" scanning (i.e. scanning that is detected by the AC detector module, as distinguished for slower stepping/scanning across a sample) may occur in 1 or 2 dimensions. A rapid 1-dimensional scan may be used across a particular interface or feature where there is a concentration gradient. A 2-dimensional scan may be used in a pattern to cover an area where there are concentration gradients. For example, a Lissajous-type scanning pattern may be used to relatively uniformly scan a 2D area of the sample (using simple control electronics). Such a pattern may be used, for example, where scanning is performed over a single cell in liquid, with various wavelengths sampled in order to deduce quantities of one or more cellular components—with the present invention ensuring that even small quantities of target compounds result in a high-contrast signal at the detector.

Beam Spot Shaping: various spot sizes and shapes may be used in the present invention, including circular spots, but also elliptical spots particularly suited for 1-dimensional scanning perpendicular to the long axis of the elliptical spot. For example, when scanning over the interface between two liquid flows in a flow chamber, an elliptical spot with a long axis parallel to the flow (and interface), and therefore perpendicular to the direction of scanning of the beam over the sample (or sample past beam) may provide particularly high contrast as the spot moves over the interface between liquids (compared to a more gradual change for a circular spot, for example). Such a configuration would be valid for transmission, transflection, or surface-sampling optical configurations such as ATR prisms integrated with the flow chamber.

Figure 7:
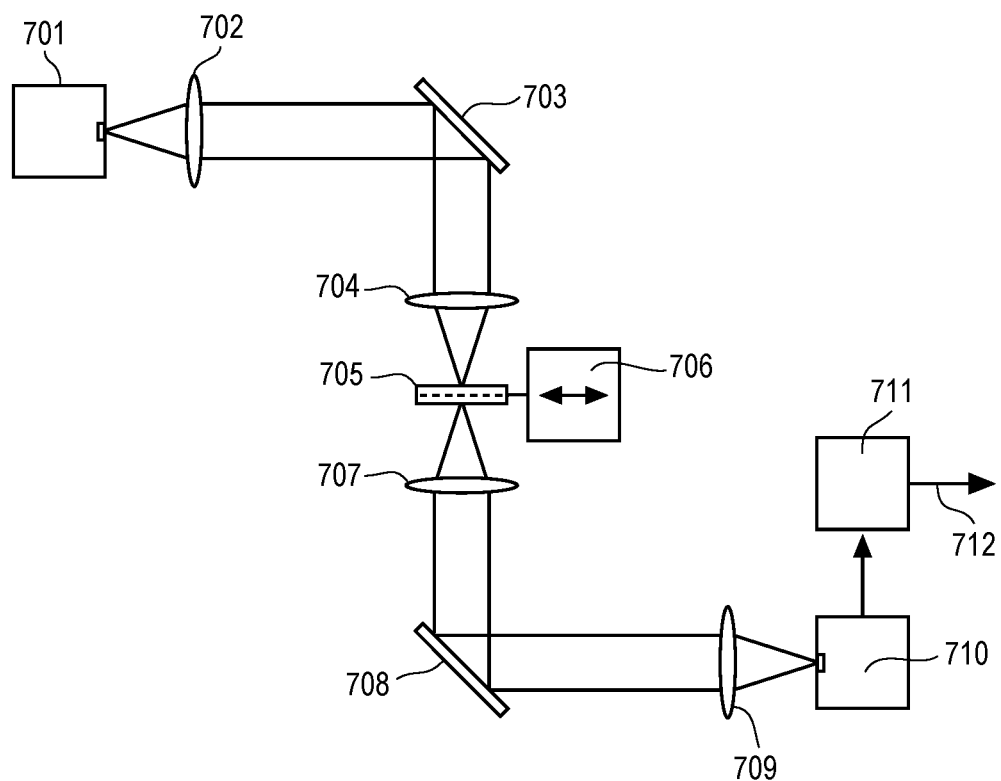

FIG. 7 shows another embodiment of the present invention; in this instance the sample chamber is scanned across the beam in order to induce modulation according to gradients within the liquid sample. An infrared laser source 701 is collimated using lens 702, scanned using scanner 703 and focused onto the sample chamber 705 using lens 704. The sample is scanned using scanning subsystem 706, which could for example be a piezo transducer (1- or 2-axis) capable of scanning the sample at >1 Hz, >10 Hz, >100 Hz or higher frequencies to achieve the signal modulation described herein. A capturing lens 707 re-collimates the beam and a mirror 708 redirects the collimated beam, which is then focused onto detector subsystem 710 by focusing lens 709. The signal from the detector subsystem is used by a computer unit 711 to calculate absorption and possibly concentrations, which go to the system output 712. There are some disadvantages to this embodiment of the system, including that the sample holder may have considerable mass and therefore require more energy to scan, and scanning may disturb the contents of the sample holder. However, the advantage is that a very consistent optical spot is maintained on the sample, reducing optical artefacts that result in non-signal modulation at the detector. In this embodiment, the sample holder may be translated both by the scanning system, as well as a secondary translation system that allows the sample to be put in focus ("Z axis"), and different portions of the sample to be measured.

Scanning Cytometer: For example, a scanning cell cytometer constructed using this embodiment may use an XYZ stage to move over a population of cells within a liquid, and at each cell, the modulating scanning function is used to scan a small area containing the cell at high frequency to cause power modulation on the detector according to wavelength and analyte concentrations within the cell. In this manner, a large population of cells may be measured, each with a very high signal contrast, allowing high-precision absorption measurements. In this case, the modulation scanning at the cell level may be achieved with either a 1-dimensional scan (possible with an elliptical beam with the long axis perpendicular to the scan axis), a 1-dimensional modulating scan with stepping in the direction perpendicular to the scan axis, to build up a profile of the cell (or integrate the absorption signal), or a 2-dimensional modulating scan which uses a pattern such as Lissajous scanning over the local region around the cell—where integration of the resulting modulating signal used to calculate absorption in the cell. In such case, an infrared laser source such as a tunable QCL could be used to sequentially scan the cell at multiple wavelengths in order to calculate contents of the cell. Alternatively, such a scanning cytometer may be built using an XYZ translation stage for rough sample positioning, and mirror-based beam scanning mechanisms (as described above) to achieve local 1- or 2-dimensional modulating scans over the neighborhood of single cells.

Figure 8:
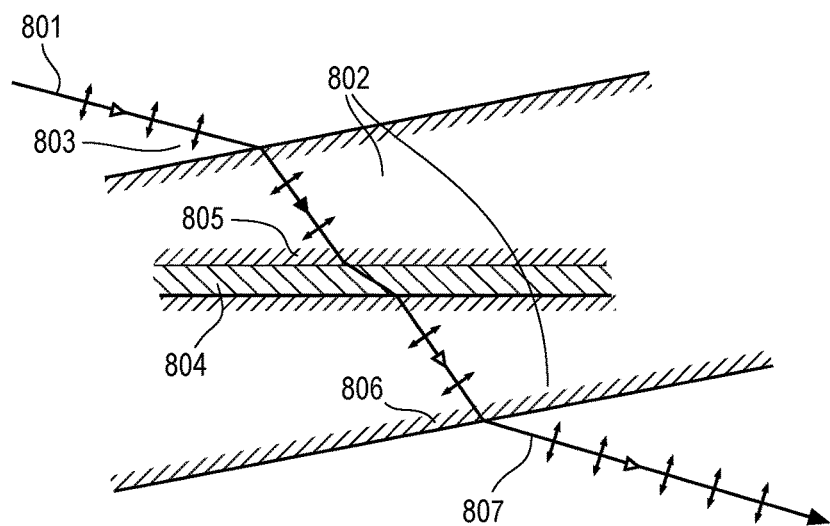
FIG. 8 depicts an example sample holder for use in the present invention.

FIG. 8 depicts an example sample holder for use in the present invention. As light from laser sources in the mid-infrared is coherent and often has narrow bandwidth (monochromatic), issues of optical interference can become problems. In the present invention, where one or more beams is scanned relative to the sample and sample holder, small changes in reflection from the interfaces of the sample holder, compounded by coherent light effects, could cause changes in intensity of the light to the detector that are not related to the sample itself; in addition, strong interference effects within the sample holder may change the effective optical power at the sample itself (standing wave effects); finally, reflections back to the laser source (optical feedback) may cause significant noise in the laser output. As a result, care should be taken to minimize changes in the optical path through the sample holder, and to minimize reflections from surfaces of this holder. The example shown in this figure consists of an infrared flow cell with surface angle at the Brewster angle, or the angle where p-polarized light is transmitted without reflection through surfaces. Mid-infrared light 801 (shown here to be p-polarized) from some mid-infrared laser sources (this is particularly true of QCLs) is highly polarized, and therefore this design may be employed without significant losses or back-reflections. The example sample holder shown here consists of two infrared-transparent windows 802 which appear on either side of a liquid sample channel 804, which may contain a stationary or flowing liquid sample. The thickness of the windows 802 is for illustrative purposes only; typically the thickness of the windows will be many times the thickness of the liquid chamber or channel. The angle of incidence 803 from the surrounding medium (typically air) into sample holder window surface is at the Brewster angle, where there is no reflection of p-polarized light; subsequent angles 805 (window-to-liquid) and 806 (window-to-air) as well as the angle exiting the liquid into the window are all constructed, based on the respective refractive indices (at the operating wavelength) of the surrounding medium, window material, and liquid sample. In this manner the transmitted light 807 is free of "ghost images" resulting from internal reflections, as well as free of "fringes" resulting from resonant cavities inside the sample holder, or between the sample holder and other system components. This is of particular importance in the present invention due to the modulation scanning of the beam over the sample, and therefore the sample holder. Such scanning may result in slight deviations of incident angle, as well as scanning over slight thickness variations within the sample holder windows, and other path length variations, that would be significantly amplified if resonant cavities were to form inside the sample holder, or between the sample holder and other system components. In the present example, the beam would be scanned in and out of the plane of the paper relative to the sample holder (or, equivalently, the sample holder is scanned), so as to keep the incident angles substantially identical throughout the scan range.

High-Frequency Laser Modulation. For semiconductor infrared laser sources such as QCLs, spectral inherent linewidths, or width of individual lasing modes emitted from the laser, can be extremely narrow (<0.01 cm-1). As a result of these narrow linewidths, resonant effects such as fringes may be very pronounced. For semiconductor-based laser sources in the infrared such as QCLs, it is often possible to "spread" the effective linewidth of the laser through the use of some current modulation, which produces a rapid thermal modulation within the laser chip, and therefore refractive index changes that result in wavelength modulation (and concomitant amplitude modulation). In an extreme case, these lasers may be operated in pulsed mode, where their spectral linewidth may spread considerably. This is important because a broader linewidth reduces the coherence length of the emitted light—or the distance over which pronounced interference effects may occur. In traditional infrared spectroscopy applications where gas is measured, narrow linewidth is prized in order to make precise measurements based on extremely narrow gas absorption lines; however in liquid-phase samples, absorption peaks typically have peak widths on the order of 5 cm-1 or more. As a result, embodiments of the present invention may include modulation or pulsing of the laser light sources in order to reduce coherent artifacts within the system. The modulation of the laser source should be done at a higher frequency than the modulating scanning described herein, and in fact, beyond the bandwidth of the primary detector used in the system. Significant thermal tuning (and therefore frequency broadening) can be achieved in QCL chips, for example, with modulating frequencies of 10-100 KHz, and even 100-1000 KHz. Additionally, some QCL chips may be pulsed at high frequency, for example 10-100 KHz and even higher. At these frequencies, thermal detectors such as pyroelectric detectors do not experience a modulated signal, but a DC average of this modulated or pulsed power; therefore none of the dynamic range of the detector or associated circuitry is consumed by the modulation or pulsing.

In the context of the present invention, it is desirable to extend distances between components where back-reflections cannot be avoided to distances beyond the coherence length of the laser source(s).

Figure 9:
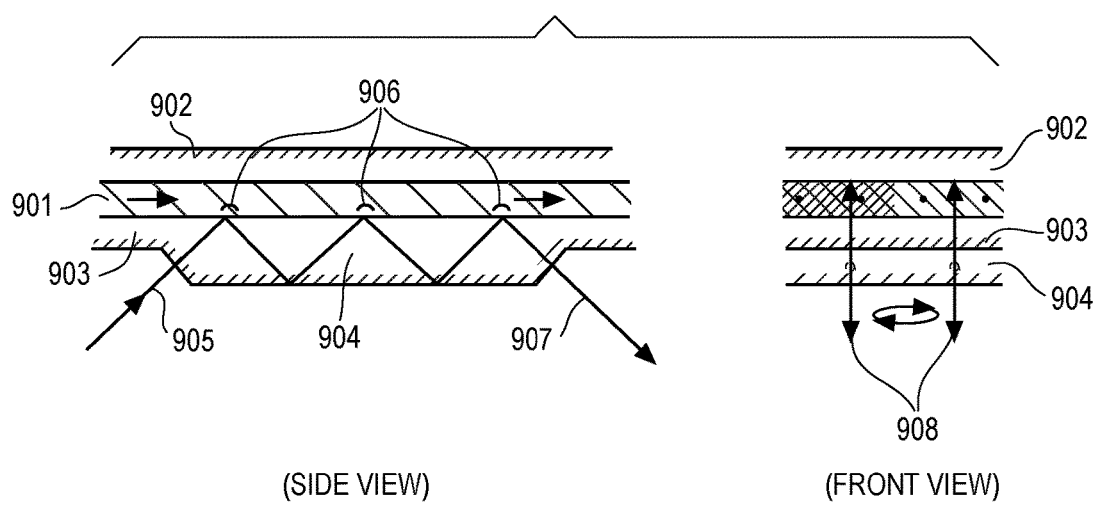
FIG. 9 shows an example of a liquid chamber/channel-integrated attenuated total reflection (ATR) prism that could be integrated into on example embodiment of the present invention.

FIG. 9 shows an example of a liquid chamber/channel-integrated attenuated total reflection (ATR) prism that could be integrated into on example embodiment of the present invention. Such a configuration may be used in applications where the liquid medium is highly absorptive (such as water, in large ranges of the mid-infrared range), but narrow liquid channels that would allow sufficient light transmission are not feasible (because of the danger of clogging, for example). Here a liquid channel 901 carrying a flow of liquid is shown; this channel is contained between two surfaces: top surface 902 which need not be transparent in the mid-infrared; and bottom surface 903 which is constructed from an infrared-transmissive material, and has an integrated ATR prism 904. Incoming infrared light 905 enters the prism (the light and entry surface may be oriented such that the entry is at the Brewster angle, as described above), and then reflects one or more times from the surface in contact with the fluid sample. With each total internal reflection from this surface, there is some evanescent penetration 906 of the light into the channel and therefore the sample, and absorption according to the wavelength, the chemical contents of the sample and their resonant infrared peaks. The transmitted, exiting light 907 is then relayed to the AC detection subsystem as described above. In this design, the beam and sample holder are scanned relative to one another in a direction perpendicular to the plane of the paper, such that the entry angle, reflection angles, and exit angles, as well as the internal distances within the prism, remain identical. A front view depicts a cross-section this from the direction in which the fluid flows, with two beams 908 showing the extremes of the scan range, and the liquid showing a concentration gradient within the range of this scan that will result in a modulation signal at the detector, depending on the incident laser wavelength. This configuration may be used, for example, where a sample liquid is flowed in parallel with a reference liquid, and the scanning beam is scanned back and forth across the interface between these liquids. Any intensity modulation in the transmitted, exiting light 907, then, indicates a differential in the contents between sample and reference liquids-providing high detection sensitivity at a frequency above low-frequency noise and system drifts. The example here, again, may be used where a transmission or transflection measurement is not appropriate, because it is physically difficult to flow the sample liquid through a narrow enough channel (due to viscosity, particulates that could cause clogs, etc.).

Figure 10A:
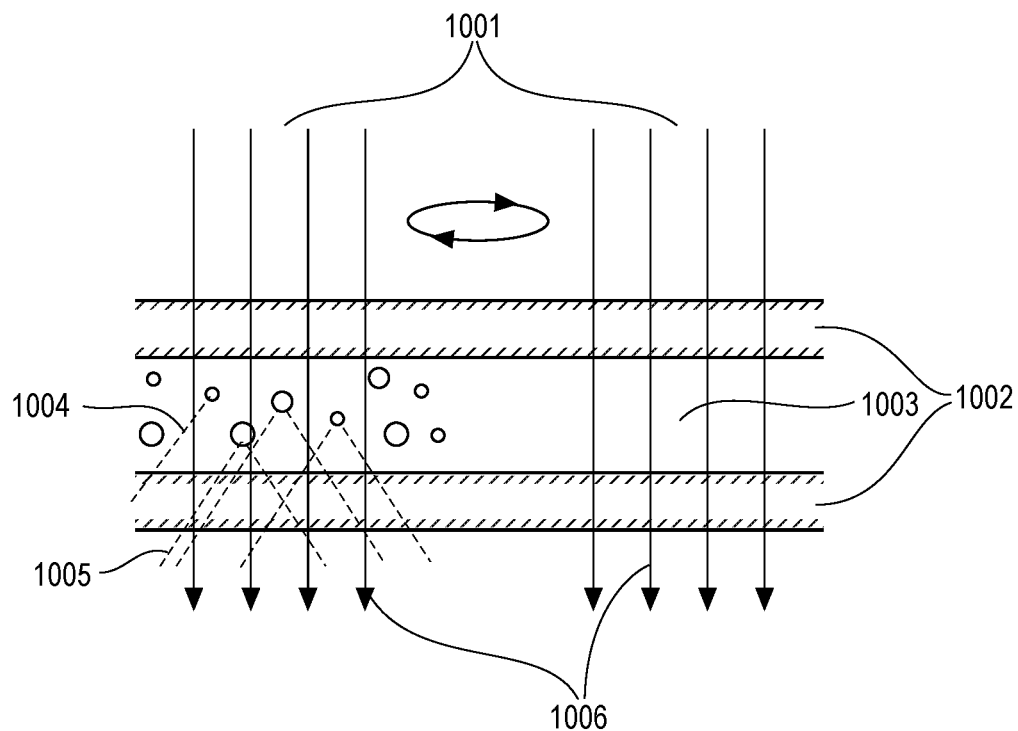
FIG. 10a shows an example of a scanned liquid sample in the present invention where the liquid includes dispersed solids or liquids.

FIG. 10a shows an example of a scanned liquid sample in the present invention where the liquid includes dispersed solids or liquids-for example hydrocarbons dispersed in a water sample, or fat droplets in milk. Two incoming infrared beam positions (the extremes of a scan range) of scanned beam 1001 are shown as they are transmitted through a liquid sample 1003 in a channel or chamber between two infrared-transmissive windows 1002. In this case, the liquid is shown to have two regions that the beam scan range straddles: one without, and one with scattering particles 1004 such as suspended solids, suspended droplets, biological cells, or other significant inclusions other than dissolved chemicals. The gradient in such inclusions could be a result, for example, of two liquids in a laminar flow (in or out of the plane of the page)—one of which is a sample (typically the one with the inclusions), and one of which is a reference liquid without inclusions, or with a known distribution of included particles or droplets. As the beam passes through regions with these inclusions, light is scattered as a function of the size and shape of the inclusions, as well as the complex refractive index of the inclusions relative to the liquid medium carrying them. As described above, specific infrared wavelengths may be used where particular chemical components of the inclusions (or the medium) have sharp rises or drops of refractive index (resonant regions), or high absorption. Thus, the ability to measure scattered light as a function of wavelength can allow calculation of various combinations of inclusion size, concentration, and chemical composition-or, be used to calculate the concentration of inclusions with a particular chemical makeup (for example, resonant Mie scattering effects at specific wavelengths could be used to measure only the concentration of droplets composed of hydrocarbons, vs gas bubbles or other inclusions in a liquid).

Figure 10B:
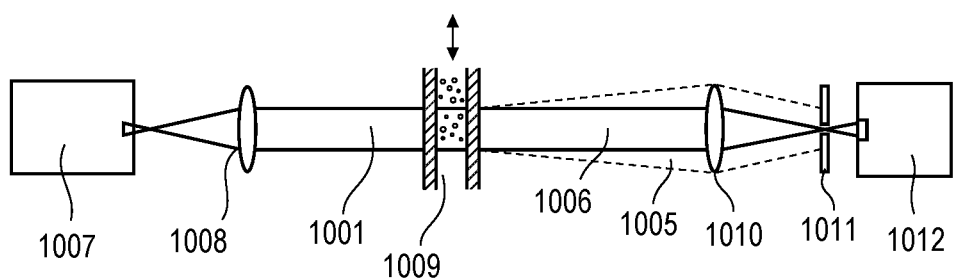

FIG. 10b shows an example of the present invention used to measure dispersed contents within the liquid sample of FIG. 10a. Light from an infrared laser source 1007 (which, as in all examples in this invention, may provide multiple wavelengths, either sequentially or simultaneously) is collimated by lens 1008 to provide a scanned beam 1001 to the liquid sample 1009. In this example, scanning modulation is achieved by scanning the sample holder with the liquid sample back and forth across the beam. Some light is transmitted directly 1006, with absorption according to concentrations of species in the liquid sample and wavelength. Light that is scattered 1005 due to inclusions in the liquid emerges with a distribution of angles dependent upon the size and chemical composition of the inclusion. In this example, a focusing lens 1010 is used to focus the directly transmitted light through a pinhole aperture in the spatial filter 1011; this aperture transmits light that passed directly through the sample with only attenuation, but preferentially blocks light that has been scattered at an angle by inclusions in the sample. The light transmitted through the pinhole aperture is then detected by a detector subsystem 1012 which is AC-coupled and designed to respond to signals at the frequency of the modulation scanning (of the sample holder past the beam). By measuring this signal as a function of wavelength, it is then possible to calculate one or more of total concentration of an analyte in the liquid, concentration of inclusions, contents of these inclusions, and/or size of the inclusions in the liquid sample.

In such scattering-measurement embodiments of the present invention, it may be desirable to directly measure scattering; for example, inverting the spatial filter 1011 to block any directly-transmitted light and measure only light scattered by the sample as it is scanned across the beam. This may be repeated at several wavelengths in order to calculate on or more of total concentration of an analyte in the liquid, concentration of inclusions, contents of these inclusions, and/or size of the inclusions in the liquid sample. In other embodiments, largely directly-transmitted light may be separated from largely scattered light by use of mirrors and/or spatial filters and measured independently and simultaneously.

FIG. 11 shows further explanation of the scattering measurement that may be employed in certain embodiments of the present invention where particles, cells, droplets or other inclusions are dispersed in the liquid sample. For each graph, the horizontal axis is optical frequency, with higher frequencies (shorter wavelengths) to the right of the graphs. Graph 1101 shows the absorbance, as a function of wavenumber, of an example compound, with a resonant absorption peak centered at $v_a$. For standard absorption measurements in the present invention, a laser source would be configured to emit infrared light corresponding to this peak, and the beam scanned over the sample containing potential gradients in concentration of this peak, resulting in a modulation of the transmitted light (as a result of the compound-specific absorption). Light one or more other wavelengths, typically nearby to the target absorption peak, may also be used to establish a "baseline" for the peak absorption measurement (i.e. cancel out other factors and overlapping absorption signatures—not shown here).

Graph 1102 shows the real refractive index of the target compound (solid line) and liquid medium (dashed line) as a function of frequency. As a result of the Kramers-Kronig relationship between real and complex refractive index, the real index of the target compound displays a "wiggle" that is a derivative of the absorbance shown above it, in addition to a constant term. In this illustration, the index of the medium is relatively constant. As a result there is relatively rapid change (with frequency) of index differential between the target compound and the medium, with a local maximum at $v_b$ and a local minimum at $v_c$. The importance of this variation in index differentials becomes clear in Graph 1103, which represents the scattering efficiency of a droplet or particle of the target compound resident in the medium. The scattering is a function of the size of the inclusion (held constant for the purpose of this illustration) vs the illuminating wavelength, as well as the refractive index differential. There is a general upward trend towards higher frequencies (shorter wavelengths), as the size of the particle becomes larger compared to the wavelength. Superimposed on this scattering "baseline" is the local variation due to the refractive index change around the resonant frequency of the compound (really specific molecular bond vibration modes within the compound). Where index differential is higher ($v_b$), scattering increases, and where it is lower ($v_c$), scattering decreases. This effect-resonant Mie scattering-occurs over a short frequency range where other factors are relatively constant. As a result, in certain embodiments of the present invention, as described above, it is possible to measure compound-specific scattering in a liquid sample. As described above, substantially directly transmitted and scattered light may be measured separately, or the combined effects may be measured, resulting in an extinction curve such as the one shown in Graph 1104. In this compound signal, one or more discrete frequency points may be used to measure the characteristics of the liquid with dissolved or dispersed components: frequencies $V_1$ and $V_2$ may be used to measure non-specific scattering from the sample (and therefore indicate, generally, the level of inclusions in the liquid); a laser at frequency $v_a$ may be used to assess absorption (at this frequency there is no net effect from resonant Mie scattering, but includes the baseline Mie scatter) alone when baselined using non-resonant scattering measurements from $v_1$ and $v_2$. Finally measurements at frequencies $v_a$ and $v_b$ may be used to extract the resonant Mie scattering effect, and therefore compound-specific scattering by inclusions in the system. These measurements, made using the scanning modulation system described in the present invention may enable high accuracy calculation of dissolved and dispersed components within a liquid sample.

Wavelengths: the present invention is primarily focused on the mid-infrared (2-20 um) wavelength range where molecules have specific resonant absorption fingerprints; furthermore the invention may be applied in the Terahertz range (100-1000 um) to which infrared laser sources have recently been extended, and where molecules likewise exhibit characteristic fingerprints. In this range, it is also possible to measure interactions between molecules, or within molecules (such as proteins, when folding) using the spectroscopic techniques described herein. The present invention may be used, for example, to scan the interface between two liquid samples that interact, providing high sensitivity to the resulting molecular interactions provided by the scanning-modulated liquid measurement system described herein.

Laser Sources: the present invention comprises infrared and Terahertz laser sources of all types—the key distinguishing features of such sources (as opposed to traditional incandescent or even synchrotron sources) being that: they provide relatively high power at specific wavelengths of interest; and they are coherent, small aperture sources that are a result may be efficiently collimated or focused onto a sample, and therefore provide relatively high optical power onto a limited area, which is then scanned to provide the modulation that is central to the invention. Specifically, quantum cascade lasers (QCLs) are a suitable source for many embodiments of the present invention, as they can be manufactured to emit light at tailored wavelengths within the mid-infrared and Terahertz bands that are the subject of the present invention. Furthermore, QCL sources may be tunable (through the use of external gratings, tunable filters, or other mechanisms) over wavelength ranges suitable for measuring resonant absorptions in liquid-phase samples; furthermore, monolithically integrated arrays of QCLs with distinct wavelengths may be fabricated, again emitting over a range suitable for liquid-phase sample measurement. All of these types may be used in the present invention. Other infrared laser sources, including $CO_2$ lasers, lead-salt lasers, optical parametric oscillators, etc. may be used in the present invention.

Example Embodiment—Hydrocarbon in Water Measurement

The present invention may be used to measure impurities in liquids, for example hydrocarbons that may be present in water as a result of hydrocarbon exploration, exploitation or processing operations. An example embodiment for this application comprises the following:

- A mid-infrared QCL source configured to emit at a frequency around a major hydrocarbon absorption band, for example 1460 cm-1. This QCL source is tunable such that it covers a range that includes the hydrocarbon absorption band, but also adjacent frequencies where hydrocarbons do not absorb as strongly (for reference levels). This QCL source may be pulsed, or modulated at high frequency (for example, 100 kHz) to spread its bandwidth and avoid some coherent artifacts in the system.
- A liquid handling system that introduces the liquid sample, along with a reference liquid (pure water) into a flow chamber where these liquids flow in laminar fashion through a measurement cavity.
- One surface of this flow chamber is bordered by an infrared-transparent window, for example CaF2 or ZnSe. This window has integrated into it a ATR prism which allows multiple internal reflections of infrared light from the surface in contact with the fluid chamber, these reflections occurring along the axis of the flow.
- Optical components to relay the infrared light from the QCL source into the ATR prism, with the center position of the reflections in the ATR being close to the interface of the sample and reference liquid flows; the entry angle into the ATR and the exit angle out of the ATR configured relative to the polarization of the QCL source such that a minimum reflection occurs at these surfaces, according to the Brewster angle calculated using the index of the ATR prism material;
- A sample scanning system that repetitively translates the sample holder and ATR in a direction perpendicular to the flow and to the sequence of reflections inside the ATR. This scanning system translates the sample and the contained flow at roughly 100 Hz, for example.
- Optics to capture relay the light emerging from the ATR prism, which has evanescently interacted with the flow in the chamber, to a detector subsystem;
- A detector subsystem which is configured to detect the transmitted infrared light, with electronics designed to isolate and amplify the signal that results from the scanning of the sample holder (and contained flow) and therefore the effect of the hydrocarbon concentration gradient at the border between the sample and reference liquid flows; further comprising a DC level detector which measures the average power transmitted through the system; for example, the AC detector in this system may be based on a pyroelectric detector (which is inherently AC-sensitive); the DC portion may be based on a thermopile detector; both of these are uncooled, stable, broadband and low-cost detectors;
- A control and computing system which:
  - tunes or switches the QCL source sequentially to wavelengths corresponding to one or more reference wavelengths (where hydrocarbon in relatively weak) and peak absorption wavelength (where hydrocarbons in question have relatively strong absorption);
  - optionally controls the modulation scanning of the beam between the sample and reference flows, within the ATR sample;
  - records the amplitude of modulation detected by the detector subsystem, as well as the DC power level transmitted through the system; normalizes the modulated power by the DC transmission;
  - calculates hydrocarbon concentration in the water by normalizing signal at peak absorption wavelength by the signal at reference wavelengths;
  - reports the hydrocarbon concentration in the sample;
  - optionally, controls the scanning or other translation mechanism to position the flow interface (between sample and reference) at the centerpoint of the beam vs sample holder scanning range;
  - optionally, occasionally positions the scanning range entirely in the reference liquid, so as to extract a baseline signal level where no concentration gradients are present;
  - optionally, stops all scanning motion and centers the beam on the flow interface to observe signal from any turbulence within the flow, adjusting flow rates appropriately to achieve laminar flow and therefore a clean interface between the two fluid streams.

This example system enables the measurement of very low levels of hydrocarbons dissolved in water samples through the use of the present invention's unique infrared laser liquid-scanning plus AC detection architecture.

Example Embodiment—Scanning Cytometer

The present invention may be configured to measure biological cells in a liquid sample between two slides—a standard format for biological research and clinical diagnostics such as inspection of cells from a pap smear for cancer. In this example, the slides are transparent to both visible and infrared light; for example they may be CaF2 windows. This example system comprises:

- a visible microscopy system which images the cell or tissue sample, which may have dyes or fluorescent labels applied to it for the purpose of increasing contrast and/or identifying certain cell characteristics;
- a translation system which allows imaging or infrared measurements of different regions, laterally, across the cell sample, and focus of the sample for both visible imaging and infrared measurement;
- a system which calculates, based on position in the visible image(s), the position of a cell with respect to a scanning infrared cytometry subsystem, so as to bring any cell identified in the visible image into focus for infrared scanning as is described in the present invention;
- a QCL source capable of emitting multiple mid-infrared wavelengths corresponding to absorption bands for molecules found in cells, such as (but not limited to) DNA, RNA, lipids, proteins, cell metabolites, cell nutrients; as well as nearby bands that serve as reference wavelengths for baseline measurements;
- optics configured to focus the QCL output through a pinhole aperture for the purpose of "cleaning up" any higher mode emissions from the QCL(s), in order to ensure a consistent, uniform spot may be focused on the sample;
- optics configured to form an elliptical spot on the sample, with a long axis perpendicular to the modulation scan direction; the elliptical spot designed to provide high contrast as the beam is scanned over a cell, but relatively uniform signal for small displacement of the beam vs the cell perpendicular to the scan axis; enabling single-axis modulation scanning of each cell;
- optics configured to scan the beam rapidly such that the spot on the sample is sufficient to scan across a single cell, perpendicular to the long axis of the elliptical spot as described above; this modulation occurring at a frequency above much of the low-frequency noise and variations in the system (for example, 100 Hz);

optics configured to capture and "de-scan" the transmitted light so that angle or position variations induced by the scanning system described above are reversed, such that light may be relayed to stationary detectors;

optics configured to split substantially light that was substantially directly transmitted through the sample (with some attenuation) from light that was substantially scattered at an angle as it passed through the sample and any cells in the infrared optical beam;

detectors configured to respond preferentially to signals at the scanning frequency, to measure signals associated with changes in transmitted light as the beam passes through a cell, and thereby local variations in infrared light absorption and/or scattering associated with the cell; at least one of these detectors configured to measure substantially transmitted light, and another one of these detectors configured to measure substantially scattered light;

a computing system configured to receive the detector outputs and calculate absorbed and scattered light from the signals;

a computing system which, based on the calculated absorption and scattering signals at different wavelengths, calculates cellular content of one or more compounds within the cell being measured;

a control system which, based on cells identified in visible images, positions the infrared scanning system at cells, tunes or switches wavelengths in the QCL source, and scans cells with the infrared beam, performing the measurements described above.

Such example system may be used in an automated diagnostic application to further inspect suspicious cells (based on visible images of dye-marked cell samples) for DNA content and/or distribution, which may identify cells as likely cancer cells based on an abnormal amount or spatial distribution of DNA or other materials.

For such cancer screening, additional measurements can be made with embodiments of the present system which measure peak frequency of DNA bond vibrations in order to measure packing density (which affects bond vibration frequencies).

Additionally, absorption/scattering peaks corresponding to specific DNA bases (cytosine, in particular) may be measured in order to estimate methylation level.

One embodiment of a scanning cytometer system utilizes the scanning system as described to inspect individual reproductive cells (gametes) in order to determine the likelihood of reproductive success and/or offspring viability for human as well as livestock reproductive medicine. The scanning cytometer is configured with mid-infrared light sources (such as QCLs) with wavelengths corresponding to critical molecular components within the gametes. For example, one or more wavelengths corresponding to DNA molecular vibrations may be utilized in order to (1) quantify the absolute amount of DNA carried by the cell using extinction (absorption and/or scattering) at the peak frequency, in order to characterize DNA base count, which may indicate aneuploidies, and may also be used in sperm cells to determine the sex of the prospective offspring using the X-Y chromosome DNA differential; (2) detect the packing density of the DNA by its spectroscopic scattering signature (resulting from differences in overall DNA mass shape and size) and/or by shifts in the frequency distribution of its absorption and/or scattering peak wavelengths (resulting from differences in stresses on the bonds being observed);

(3) the level of DNA methylation in the cell, as an indicator of potential epigenetic factors.

These methods, besides being applied pre-fertilization to gametes, may be applied to Zygotes and embryos in order to profile them and predict reproductive success as well as the success of an offspring. DNA-specific measurements, together with non-DNA measurements to characterize other components of the embryo, as well as density, size, shape, may be used to select specific embryos for implantation.

Scanning Flow Cytometry System

Embodiments of the present invention that use a scanning beam interrogating a flow in order to measure single particles or cells are also possible. For example, a microfluidic flow cell may be used to create a laminar flow containing a core stream surrounded by a sheath stream, with the core stream containing particles or cells. A beam is focused on the area surrounding this core stream. The beam may be shaped such that it is asymmetrical.

In such a configuration the beam will typically be scanned at a frequency that allows multiple passes over each particle as it transits the interrogation region, allowing the signals corresponding to absorption or scattering to be isolated with high signal to noise. Depending on the shape of the beam, additional information about the shape of the particle may be extracted from the scan signal or resulting signal envelope.

In some embodiments of the present invention, it may be desirable to employ two or more scanners to direct beams of different wavelengths, at two or more different frequencies that may be clearly separated electronically after detection, using appropriate bandpass filtering.

In other cases, spots of different wavelengths may be scanned simultaneously, but offset from each other in a manner that allows separation in after detection.

Time-Resolved Measurements

The present invention is particularly useful for time-resolved measurements of particles, cells, or groups of cells (including embryos). The advantage of a scanning cytometry system, of course, is that repeated measurements of single or multiple cells may be made to track changes over time, including changes in: chemical composition and concentrations, molecular conformation/folding/condensation, number of cells in a particle, volume, shape, density, and orientation.

However one known problem with time-resolved measurements in conventional scanning cytometry is photobleaching and other photodamage. Photobleaching results from repeated exposure to excitation wavelengths used to excite fluorescent dyes and labels—leading to lower fluorescent response and therefore inaccurate measurements. Moreover, the short wavelengths often used as excitation wavelengths may cause direct ionization damage to the particle, cell, embryo or organism under observation. Finally, dye- and label-based measurements suffer from the fact that concentration or effectiveness of these external chemicals may vary over time and depending on local condition, causing further errors in measurements.

The present invention enables time-resolved measurements without these problems, and therefore without their negative effects on accuracy. The present invention uses mid-infrared radiation, allowing direct measurements of chemical concentrations and conformation, and associated measurements such as non-water cell volume, shape, etc.— all without external labels or dyes. Therefore there is no dependence on labels that may photobleach or change in effectiveness/concentration over a time series measurement. Furthermore, the very low energy of the radiation used in the present invention precludes any ionization, and therefore removes any question of cellular damage due to interrogating radiation.

A number of time-resolved measurements may be made with the present invention, including but not limited to drug-cell interactions (including drug uptake, drug efflux), metabolic measurements, cell division, apoptosis, chromatin condensation, cell-cell interactions, embryo growth, lipid and other product generation, internal protein changes, changes in local chemical environment as a result of cell activity, and shape, volume, density, and cell count changes.

Example Embodiment—Drug/Cell Interaction Measurement

The present invention may be used to measure drug interactions with cells, for example the effects of drugs on cancer cells. In such an embodiment, cells would be placed in a plate containing multiple individual wells into which nutrients as well as drugs are placed. These cells are scanned using one or more mid-infrared wavelengths corresponding to specific compounds within the cells, for example nucleic acids, proteins, lipids, or metabolic products. Typically, there will be additional wavelengths that act as "reference" wavelengths—to eliminate cross-effects from other compounds, or to eliminate effects from changes in cell shape or volume. A wide range of wavelengths may be used (employing one or more tunable quantum cascade lasers, for example) to measure the cells, using scanning, over a broad spectrum, and then known data techniques such as principal component analysis, or new methods such as "deep learning" neural networks, may be used to classify changes in cells. In such a manner, changes in cell populations responding to drugs may be classified with high accuracy, and without labels or dyes that could disturb cell behavior, or create their own sources of error over time, as described above.

In such an embodiment, the scanning system described herein may additionally be used to measure the relative concentration inside and outside of the cell of one or more compounds, for example to measure uptake of a compound, or efflux of a compound into the well containing the cell. Such compounds could include drugs, nutrients, metabolic products, or others. Because of the scanning nature of the present invention, the signal (at a particular wavelength) will be proportional to the relative extinction (absorption and scattering), and therefore can give relative concentration measurements between the cell(s) and its(their) local environment. For example, at a certain point in the measurement series, a compound could be added to the cell, and the time required for the concentration within the cell(s) to rise could be measured using the present invention.

Example Embodiment—Embryo Monitoring and Scoring

In on embodiment of the present invention, the scanning system is used to score individual embryos for potential implantation in human or animal reproductive medicine. In in-vitro fertilization (IVF) procedures it is preferable to implant a minimum number of embryos to avoid multiple births, and therefore to select the most viable embryos for implantation. Current selection procedures are very limited because they must minimize damage to the embryo, and therefore use of dyes or labels (or excitation lasers with high photon energy) is not advisable. As a result, selection technologies are centered primarily on visible imaging (whether with a human viewer or an automated image processing algorithm), or measurements of the medium in which the embryos reside to measure uptake or nutrients and/or metabolic products. There is no ability to directly measure chemical changes within embryos, or a chemical-structural changes (for example, nuclear content/activity separate from other cellular components).

The present invention allows direct measurement of the chemical composition and evolution of the candidate embryo over the first days of growth, and therefore a far larger range of parameters of the embryo may be observed: chemical composition; structure; and combination of chemistry and structure through resonant scattering measurements.

Scattering and Resonant Scattering Measurement

In a resonant scattering measurement, infrared wavelengths around absorption peaks of specific molecules are used in scattering/angle deflection measurements; at these wavelengths, the refractive index of these molecules varies (in accordance with the Kramers-Kronig relationship); therefore particles or cells will refract light differently at specific wavelengths in accordance with chemical composition as well as structure. Such chemical-specific (resonant) scattering is known as resonant Mie scattering.

Scattering may be measured in the present invention through the use of spatial masks in the illuminating beams that block directly-transmitted light from a detector; they may in addition use spatial masks to limit the angle distribution of the incoming light to the sample, and then another spatial mask to sample specifically those angles where light was blocked after the sample; any light in the output will then be a result of scattering from the sample. The scattering signal will, in accordance with the present invention, be present in the detector at a specific frequency, and therefore may be isolated with high signal-to-noise ratio. Depending on the wavelengths employed and angles measured, this configuration of the present invention may measure particle/cell shape, volume, density and also chemical-specific volume, density and packing information.

Example Embodiment—Sperm Diagnostics and Selection

For human fertility treatments as well as livestock breeding it is often desirable to measure sperm cell parameters to perform diagnostics and/or select individual cells for fertilization. An embodiment of the present invention may be used to first map a large number of cells in a sample container (using a scanning beam and/or translation of the container), and then to measure individual cells, for diagnostics as well as selection.

In such a system, the beam may be scanned over the cell in a pattern that allows chemical/structural information (such as DNA amount, for ploidy and X/Y information, DNA packing, DAN alpha/beta configuration, DNA methylation, cell volume and shape) to be measured, but also allows the system to measure, based on the timing of the resulting signal, the relative position of the cell to the center of the scan pattern, and thereby allows a control system to track the cell with the beam as the cell moves through the sample chamber. This ultimately allows an accurate measurement of a moving cell, and at the same time allows measurement of the progressive motility of the cell, another important marker for sperm cell viability.

Alternative Scanning Mechanisms

The present invention may use conventional electromechanical methods, such as galvanometers, to scan the beam over the sample. It may also employ solid-state methods, such as the use of modulators, including but not limited to acousto-optic modulators or deflectors that use RF signals to tune diffractive patterns in a material and thereby deflect a beam passing through it. The present invention may also use fixed diffraction gratings, which when the incident wavelength is changed, diffract light at different angles. In such a configuration, slight modulation of the source wavelength (for example, thermal modulation of a QCL) would cause slight deflections of the beam coming into a sample, and thereby provide the scanning mechanism in the present invention.

Scanning mechanisms may provide either continuous scan patterns (such as a sine wave) or discrete point scanning (as might be the case with an acousto-optic deflector which deflects a beam to discrete angles). In the discrete case, typically one position would correspond to the sample under measurements, and another position would correspond to the reference medium surrounding the sample.

Beam Shaping

As described, the present invention may employ a range of scanning patterns, including 1- and 2-dimensional scan patterns. In addition, the present invention may employ various shapes of beam cross-section ("spot") at the sample location. For example, if a 1-dimensional scan is used to scan a particle, a spot with a relatively small diameter along the axis of the scan, and relatively long diameter in the perpendicular axis may be used, in order to get maximum contrast while scanning over the particle while preserving uniform sampling of the particle in the other direction (making the measurement more position-independent).

While various embodiments have been particularly shown and described, it will be understood by those skilled in the art that various changes in form and details may be made therein without departing from the scope of the invention as defined by the appended claims.

What is claimed is:

1. An analyzer of a component, comprising:
   an optical source configured to emit a first light;
   a scanning system configured to scan the first light over the component in liquid and a reference liquid flowing in parallel with the component in liquid in a flow chamber;
   wherein the scanning system scans across an interface between the parallel flows;
   wherein the parallel flows are at nearly identical pressure;
   an optical detector subsystem configured to measure a second light after interaction with the component in liquid and the reference liquid; and
   a guiding system configured to guide the first light from the optical source to the component in liquid and the reference liquid and to guide the second light from the component in liquid and the reference liquid to the optical detector subsystem.

2. The analyzer of claim 1, further comprising an interrogation region disposed on a beam path defined between the optical source and the optical detector subsystem, which is a closed, liquid-based environment at the time of interrogation and contains the component; wherein the component is a particle or a cell; and a processor that calculates a characteristic of the component based on the measured light.

3. The analyzer of claim 2, wherein the interrogation region has a thickness of about less than 1 mm.

4. The analyzer of claim 3, wherein the interrogation region has a thickness of about less than 50 µm.

5. The analyzer of claim 4, wherein the interrogation region has a thickness of about less than 10 µm.

6. The analyzer of claim 1, wherein the optical detector subsystem is configured to respond at a scanning frequency to measure transmitted light as the first light passes through the component to become the second light or to measure scattered light associated with the first light passes by the component.

7. The analyzer of claim 6, wherein the quantum cascade laser is in a form selected from the list consisting of discrete narrowband single-wavelength device; broadband emitter, such as Fabry-Peort, which may optionally be combined with a wavelength-selective or dispersive element to select a specific wavelength band; a wavelength tunable subsystem; and a QCL array which may emit a number of wavelengths from a single-chip device.

8. The analyzer of claim 1, wherein the optical source is a quantum cascade laser (QCL) which emits the first light of at least one wavelength.

9. The analyzer of claim 1, wherein the optical source emits the first light of mid-infrared or THz range; wherein the first light has at least one wavelength or multiple wavelengths; and wherein number of wavelengths can be controlled.

10. The analyzer of claim 1, wherein the scanning system scans the component in a medium inclusive of the surrounding area of the component in a 1-dimensional format or a 2-dimensional format.

11. The analyzer of claim 10, wherein the 2-dimensional format comprises a Lissajous-type scanning pattern.

12. The analyzer of claim 1, wherein the detector is an inherently change-sensitive detector that measures transmitted or scattered light between the component and a medium at at least one wavelength; and wherein the detector detects frequencies introduced by the scanning system.

13. The analyzer of claim 12, wherein the inherently change-coupled detector is selected from the group consisting of a photon detector, a thermal detector such as a thermopile, and a photovoltaic detector such as a cooled or uncooled InGaAs or HgCdTe detectors.

14. The analyzer of claim 1, wherein the scanning system has a scan rate that can be adjusted to optimize for signal-to-noise ratio.

15. The analyzer of claim 1, wherein the scanning system further comprises an XYZ stage that moves over a plurality of components in a medium; wherein as the XYZ stage moves over the plurality of components in a medium, the scanning system scans an area containing the individual component among the plurality of components.

16. The analyzer of claim 15, wherein the characteristic is concentration.

17. The analyzer of claim 1, wherein the optic source is a single fixed-wavelength laser capable of interrogating a specific absorption peak of the component in a medium; and wherein when the light is scanned between the component and the medium, the magnitude of the change detected by the optical detector allows for calculation of a characteristic of the component in the medium.

18. The analyzer of claim 1, wherein the optic source is a plurality of lasers that emit multiple wavelengths comprising at least one signal wavelength capable of interrogating the component at an absorption peak and at least one reference wavelength.

19. The analyzer of claim 17 or 18, wherein the laser is wavelength-tunable.

20. The analyzer of claim 17 or 18, wherein the laser is a broadband laser, such as a Fabry-Perot laser and wherein the multiple wavelengths are separated before detection.

21. The analyzer of claim 18, wherein the multiple wavelengths are separated after transmission through the sample fluid by a film filter or by diffraction grating.

22. The analyzer of claim 18, wherein the multiple wavelengths are modulated so that their signals are separable in the optic detector.

23. The analyzer of claim 1, wherein the first light can have wavelengths in the infrared range comprising the near-infrared region (0.75-1.4 μm), the short-wave infrared region (1.4-3 μm), the mid-wavelength infrared region (3-8 μm), far-infrared region (20-1000 μm) or the THz range.

24. The analyzer of claim 1, further comprising slides, wherein the component is disposed between the slides;
   a visible microscopy system which provides images of the component;
   a translation system which provides imaging or infrared measurements of different areas across the component and permitting focusing of the different areas of component for both visible imaging and infrared measurement;
   a focusing system which based on position of a visible image of the component brings the component into focus for infrared scanning;
   wherein the optical source is a QCL capable of emitting multiple mid-infrared wavelengths; and
   a computing system.

25. The analyzer of claim 24, further comprising optics configured to focus the light from the QCL through a pinhole aperture to ensure a consistent uniform spot focused on the component.

26. The analyzer of claim 24, further comprising
   optics configured to form an elliptical spot on the component, with a long axis perpendicular to the scan direction, and configured to scan the beam rapidly such that the elliptical spot on the component is sufficient to scan across a single component.

27. The analyzer of claim 24, further comprising
   optics configured to capture and "de-scan" the transmitted light so that angle or position variations induced by the scanning system described above are reversed, such that light may be relayed to the optical detector subsystem that is stationary.

28. The analyzer of claim 24, further comprising
   optics configured to split the first light that is substantially directly transmitted through the component to become the second light from the first light that is substantially scattered at an angle as the first light passes by the component.

29. The analyzer of claim 24, wherein the computing system is configured to receive outputs from the optical detection subsystem and calculates absorbed or scattered light and determine a characteristic of the component.

30. The analyzer of claim 24, further comprising
   a control system that based on the component identified in a visible image, positions the scanning system at the component, sets wavelength for the first light of the optical source, scan the component with the first light, and performs measurements.

31. The analyzer of claim 1, wherein the component is a gamete.

32. The analyzer of claim 1, wherein the scanning is performed without external labels or dyes.

33. The analyzer of claim 1, wherein the angle of incidence between the light and surface of the component in a medium can be adjusted to decrease surface reflections or destructive interference.

34. The analyzer of claim 1, wherein the first light and the second light having interacted with the component in liquid and the first light and the second light having interacted with the reference liquid are interfered.

\* \* \* \* \*